(12) United States Patent
Ikeda et al.

(10) Patent No.: US 7,741,081 B2
(45) Date of Patent: Jun. 22, 2010

(54) PROCESS FOR PRODUCING L-ARGININE, L-ORNITHINE OR L-CITRULLINE

(75) Inventors: Masato Ikeda, Nagano (JP); Tetsuo Nakano, Tokyo (JP); Satoshi Mitsuhashi, Machida (JP); Mikiro Hayashi, Machida (JP); Kenji Tanaka, Hofu (JP)

(73) Assignee: Kyowa Hakko Bio Co., Ltd., Tokyo (JP)

( * ) Notice: Subject to any disclaimer, the term of this patent is extended or adjusted under 35 U.S.C. 154(b) by 463 days.

(21) Appl. No.: 11/575,805

(22) PCT Filed: Sep. 28, 2005

(86) PCT No.: PCT/JP2005/017877

§ 371 (c)(1), (2), (4) Date: Mar. 22, 2007

(87) PCT Pub. No.: WO2006/035831

PCT Pub. Date: Apr. 6, 2006

(65) Prior Publication Data

US 2009/0123980 A1 May 14, 2009

(30) Foreign Application Priority Data

Sep. 28, 2004 (JP) ............................. 2004-280855

(51) Int. Cl.
C12P 13/10 (2006.01)
C12N 9/12 (2006.01)
C12N 1/20 (2006.01)
C12N 15/00 (2006.01)
C07H 21/04 (2006.01)

(52) U.S. Cl. .................. 435/114; 435/194; 435/252.32; 435/320.1; 536/23.2

(58) Field of Classification Search ........................ None
See application file for complete search history.

(56) References Cited

U.S. PATENT DOCUMENTS 5,017,482 A 5/1991 Katsumata et al.

2002/0045223 A1 4/2002 Suga et al.

FOREIGN PATENT DOCUMENTS

EP 0 259 858 A2 3/1988
JP 63-079597 4/1988
JP 2002-051790 2/2002

OTHER PUBLICATIONS

Llácer et al. Curr Opin Struct Biol. Dec. 2008;18(6):673-81. Epub Nov. 27, 2008.*
Database Uniprot, Accession No. P59295, 2003.
Database Uniprot, Accession No. Q9L1A3, 2000.
Database Uniprot, Accession No. P73326, 1997.
Database Uniprot, Accession No. Q8FTN3, 2003.
Database Uniprot, Accession No. Q6NHG8, 2004.
Database Uniprot, Accession No. Q5YYF7, 2004.
Yoshida, et al., "Mechanism of L-Arginine Production by L-Arginine-Producing Mutants of Corynebacterium glutamicum," Agric. Biol. Chem., vol. 43, No. 1 (1979) pp. 105-111.
Udaka, "Pathway-Specific Pattern of Control of Arginine Biosynthesis in Bacteria," Journal of Bacteriology, vol. 91, No. 2 (1966), pp. 617-621.
Nakayama, et al., "Fermentative production of L-Arginine," Agr. Biol. Chem., vol. 36, No. 10 (1972), pp. 1675-1684.
Nishio, et al., "Comparative Complete Genome Sequence Analysis of the Amino Acid Replacements Responsible for the Thermostability of Corynebacterium Efficiens", Genome Research, vol. 13 (2003), pp. 1572-1579.
Cerdeno-Tarraga, et al., "The Complete Genome Sequence and Analysis of Corynebacterium Diphtheriae NCTC 13129," Nucleic Acids Research, vol. 31, No. 22 (2003), pp. 6516-6523.
Ishikawa, et al., "The Complete Genomic Sequence of Nocardia Farcinica IFM 10152", Proc. Natl. Acad. Sci. U.S.A., vol. 101, No. 41 (2004), pp. 14925-14930.

* cited by examiner

Primary Examiner—Christian L Fronda
(74) Attorney, Agent, or Firm—Fitzpatrick, Cella, Harper & Scinto

(57) ABSTRACT

The present invention provides a polypeptide which has: (i) an amino acid sequence wherein one or more amino acid residues are substituted in the region at positions 20 to 38 from the N terminus of the amino acid sequence shown in SEQ ID NO: 1; or (ii) an amino acid sequence wherein one or more amino acid residues are substituted in the region at positions 20 to 38 from the N terminus of the amino acid sequence shown in SEQ ID NO: 1 and one or more amino acid residues are deleted, substituted or added in the region at positions 1 to 19 or 39 to 294; and which has N-acetylglutamate kinase activity.

10 Claims, No Drawings

SEQUENCE LISTING

<160> NUMBER OF SEQ ID NOS: 32

<210> SEQ ID NO 1
<211> LENGTH: 294
<212> TYPE: PRT
<213> ORGANISM: Corynebacterium glutamicum ATCC13032

<400> SEQUENCE: 1

Leu Gln His Phe Arg Asp Lys Ile Val Val Val Lys Tyr Gly Gly Asn

-continued

```
              1               5              10              15
         Ala Met Val Asp Asp Leu Lys Ala Ala Phe Ala Ala Asp Met Val
                          20                  25                  30

Phe Leu Arg Thr Val Gly Ala Lys Pro Val Val Val His Gly Gly Gly
                      35                  40                  45

Pro Gln Ile Ser Glu Met Leu Asn Arg Val Gly Leu Gln Gly Glu Phe
                  50                  55                  60

Lys Gly Gly Phe Arg Val Thr Thr Pro Glu Val Met Asp Ile Val Arg
          65                  70                  75                  80

Met Val Leu Phe Gly Gln Val Gly Arg Asp Leu Val Gly Leu Ile Asn
                          85                  90                  95

Ser His Gly Pro Tyr Ala Val Gly Thr Ser Gly Glu Asp Ala Gly Leu
                         100                 105                 110

Phe Thr Ala Gln Lys Arg Met Val Asn Ile Asp Gly Val Pro Thr Asp
                     115                 120                 125

Ile Gly Leu Val Gly Asp Ile Ile Asn Val Asp Ala Ser Ser Leu Met
                 130                 135                 140

Asp Ile Ile Glu Ala Gly Arg Ile Pro Val Val Ser Thr Ile Ala Pro
         145                 150                 155                 160

Gly Glu Asp Gly Gln Ile Tyr Asn Ile Asn Ala Asp Thr Ala Ala Gly
                         165                 170                 175

Ala Leu Ala Ala Ala Ile Gly Ala Glu Arg Leu Leu Val Leu Thr Asn
                     180                 185                 190

Val Glu Gly Leu Tyr Thr Asp Trp Pro Asp Lys Ser Ser Leu Val Ser
                 195                 200                 205

Lys Ile Lys Ala Thr Glu Leu Glu Ala Ile Leu Pro Gly Leu Asp Ser
         210                 215                 220

Gly Met Ile Pro Lys Met Glu Ser Cys Leu Asn Ala Val Arg Gly Gly
         225                 230                 235                 240

Val Ser Ala Ala His Val Ile Asp Gly Arg Ile Ala His Ser Val Leu
                         245                 250                 255

Leu Glu Leu Leu Thr Met Gly Gly Ile Gly Thr Met Val Leu Pro Asp
                     260                 265                 270

Val Phe Asp Arg Glu Asn Tyr Pro Glu Gly Thr Val Phe Arg Lys Asp
                 275                 280                 285

Asp Lys Asp Gly Glu Leu
                 290

<210> SEQ ID NO 2
<211> LENGTH: 882
<212> TYPE: DNA
<213> ORGANISM: Corynebacterium glutamicum ATCC13032

<400> SEQUENCE: 2 ttg cag cac ttc cgc gac aag att gtt gtc gtg aaa tat ggc gga aac       48
Leu Gln His Phe Arg Asp Lys Ile Val Val Val Lys Tyr Gly Gly Asn
  1               5                  10                  15 gcc atg gtg gat gat gat ctc aag gct gct ttt gct gcc gac atg gtc       96
Ala Met Val Asp Asp Asp Leu Lys Ala Ala Phe Ala Ala Asp Met Val
                 20                  25                  30 ttc ttg cgc acc gtg ggc gca aaa cca gtg gtg gtg cac ggt ggt gga      144
Phe Leu Arg Thr Val Gly Ala Lys Pro Val Val Val His Gly Gly Gly
             35                  40                  45 cct cag att tct gag atg cta aac cgt gtg ggt ctc cag ggc gag ttc      192
Pro Gln Ile Ser Glu Met Leu Asn Arg Val Gly Leu Gln Gly Glu Phe
         50                  55                  60
```

```
aag ggt ggt ttc cgt gtg acc act cct gag gtc atg gac att gtg cgc      240
Lys Gly Gly Phe Arg Val Thr Thr Pro Glu Val Met Asp Ile Val Arg
 65                  70                  75                  80 atg gtg ctc ttt ggt cag gtc ggt cgc gat tta gtt ggt ttg atc aac      288
Met Val Leu Phe Gly Gln Val Gly Arg Asp Leu Val Gly Leu Ile Asn
                 85                  90                  95 tct cat ggc cct tac gct gtg gga acc tcc ggt gag gat gcc ggc ctg      336
Ser His Gly Pro Tyr Ala Val Gly Thr Ser Gly Glu Asp Ala Gly Leu
            100                 105                 110 ttt acc gcg cag aag cgc atg gtc aac atc gat ggc gta ccc act gat      384
Phe Thr Ala Gln Lys Arg Met Val Asn Ile Asp Gly Val Pro Thr Asp
        115                 120                 125 att ggt ttg gtc gga gac atc att aat gtc gat gcc tct tcc ttg atg      432
Ile Gly Leu Val Gly Asp Ile Ile Asn Val Asp Ala Ser Ser Leu Met
    130                 135                 140 gat atc atc gag gcc ggt cgc att cct gtg gtc tct acg att gct cca      480
Asp Ile Ile Glu Ala Gly Arg Ile Pro Val Val Ser Thr Ile Ala Pro
145                 150                 155                 160 ggc gaa gac ggc cag att tac aac att aac gcc gat acc gca gca ggt      528
Gly Glu Asp Gly Gln Ile Tyr Asn Ile Asn Ala Asp Thr Ala Ala Gly
                165                 170                 175 gct ttg gct gca gcg att ggt gca gaa cgc ctg ctg gtt ctc acc aat      576
Ala Leu Ala Ala Ala Ile Gly Ala Glu Arg Leu Leu Val Leu Thr Asn
            180                 185                 190 gtg gaa ggt ctg tac acc gat tgg cct gat aag agc tca ctg gtg tcc      624
Val Glu Gly Leu Tyr Thr Asp Trp Pro Asp Lys Ser Ser Leu Val Ser
        195                 200                 205 aag atc aag gcc acc gag ctg gag gcc att ctt ccg gga ctt gat tcc      672
Lys Ile Lys Ala Thr Glu Leu Glu Ala Ile Leu Pro Gly Leu Asp Ser
    210                 215                 220 ggc atg att cca aag atg gag tct tgc ttg aac gcg gtg cgt ggg gga      720
Gly Met Ile Pro Lys Met Glu Ser Cys Leu Asn Ala Val Arg Gly Gly
225                 230                 235                 240 gta agc gct gct cat gtc att gac ggc cgc atc gcg cac tcg gtg ttg      768
Val Ser Ala Ala His Val Ile Asp Gly Arg Ile Ala His Ser Val Leu
                245                 250                 255 ctg gag ctt ttg acc atg ggt gga att ggc acg atg gtg ctg ccg gat      816
Leu Glu Leu Leu Thr Met Gly Gly Ile Gly Thr Met Val Leu Pro Asp
            260                 265                 270 gtt ttt gat cgg gag aat tat cct gaa ggc acc gtt ttt aga aaa gac      864
Val Phe Asp Arg Glu Asn Tyr Pro Glu Gly Thr Val Phe Arg Lys Asp
        275                 280                 285 gac aag gat ggg gaa ctg                                              882
Asp Lys Asp Gly Glu Leu
    290
```

<210> SEQ ID NO 3
<211> LENGTH: 294
<212> TYPE: PRT
<213> ORGANISM: Corynebacterium glutamicum

<400> SEQUENCE: 3

```
Leu Gln His Phe Arg Asp Lys Ile Val Val Lys Tyr Gly Gly Asn
  1               5                  10                  15

Ala Met Val Asp Asp Leu Lys Ala Val Phe Ala Ala Asp Met Val
                 20                  25                  30

Phe Leu Arg Thr Val Gly Ala Lys Pro Val Val His Gly Gly Gly
         35                  40                  45

Pro Gln Ile Ser Glu Met Leu Asn Arg Val Gly Leu Gln Gly Glu Phe
```

-continued

```
                     50                  55                  60
Lys Gly Gly Phe Arg Val Thr Thr Pro Glu Val Met Asp Ile Val Arg
 65                  70                  75                  80

Met Val Leu Phe Gly Gln Val Gly Arg Asp Leu Val Gly Leu Ile Asn
                 85                  90                  95

Ser His Gly Pro Tyr Ala Val Gly Thr Ser Gly Glu Asp Ala Gly Leu
             100                 105                 110

Phe Thr Ala Gln Lys Arg Met Val Asn Ile Asp Gly Val Pro Thr Asp
             115                 120                 125

Ile Gly Leu Val Gly Asp Ile Ile Asn Val Asp Ala Ser Ser Leu Met
        130                 135                 140

Asp Ile Ile Glu Ala Gly Arg Ile Pro Val Val Ser Thr Ile Ala Pro
145                 150                 155                 160

Gly Glu Asp Gly Gln Ile Tyr Asn Ile Asn Ala Asp Thr Ala Ala Gly
                165                 170                 175

Ala Leu Ala Ala Ala Ile Gly Ala Glu Arg Leu Leu Val Leu Thr Asn
            180                 185                 190

Val Glu Gly Leu Tyr Thr Asp Trp Pro Asp Lys Ser Ser Leu Val Ser
        195                 200                 205

Lys Ile Lys Ala Thr Glu Leu Glu Ala Ile Leu Pro Gly Leu Asp Ser
    210                 215                 220

Gly Met Ile Pro Lys Met Glu Ser Cys Leu Asn Ala Val Arg Gly Gly
225                 230                 235                 240

Val Ser Ala Ala His Val Ile Asp Gly Arg Ile Ala His Ser Val Leu
                245                 250                 255

Leu Glu Leu Leu Thr Met Gly Gly Ile Gly Thr Met Val Leu Pro Asp
            260                 265                 270

Val Phe Asp Arg Glu Asn Tyr Pro Glu Gly Thr Val Phe Arg Lys Asp
        275                 280                 285

Asp Lys Asp Gly Glu Leu
    290

<210> SEQ ID NO 4
<211> LENGTH: 882
<212> TYPE: DNA
<213> ORGANISM: Corynebacterium glutamicum

<400> SEQUENCE: 4 ttg cag cac ttc cgc gac aag att gtt gtc gtg aaa tat ggc gga aac     48
Leu Gln His Phe Arg Asp Lys Ile Val Val Val Lys Tyr Gly Gly Asn
  1               5                  10                  15 gcc atg gtg gat gat gat ctc aag gct gtt ttt gct gcc gac atg gtc     96
Ala Met Val Asp Asp Asp Leu Lys Ala Val Phe Ala Ala Asp Met Val
                 20                  25                  30 ttc ttg cgc acc gtg ggc gca aaa cca gtg gtg gtg cac ggt ggt gga    144
Phe Leu Arg Thr Val Gly Ala Lys Pro Val Val Val His Gly Gly Gly
             35                  40                  45 cct cag att tct gag atg cta aac cgt gtg ggt ctc cag ggc gag ttc    192
Pro Gln Ile Ser Glu Met Leu Asn Arg Val Gly Leu Gln Gly Glu Phe
         50                  55                  60 aag ggt ggt ttc cgt gtg acc act cct gag gtc atg gac att gtg cgc    240
Lys Gly Gly Phe Arg Val Thr Thr Pro Glu Val Met Asp Ile Val Arg
 65                  70                  75                  80 atg gtg ctc ttt ggt cag gtc ggt cgc gat tta gtt ggt ttg atc aac    288
Met Val Leu Phe Gly Gln Val Gly Arg Asp Leu Val Gly Leu Ile Asn
                 85                  90                  95
```

-continued

```
tct cat ggc cct tac gct gtg gga acc tcc ggt gag gat gcc ggc ctg      336
Ser His Gly Pro Tyr Ala Val Gly Thr Ser Gly Glu Asp Ala Gly Leu
            100                 105                 110 ttt acc gcg cag aag cgc atg gtc aac atc gat ggc gta ccc act gat      384
Phe Thr Ala Gln Lys Arg Met Val Asn Ile Asp Gly Val Pro Thr Asp
        115                 120                 125 att ggt ttg gtc gga gac atc att aat gtc gat gcc tct tcc ttg atg      432
Ile Gly Leu Val Gly Asp Ile Ile Asn Val Asp Ala Ser Ser Leu Met
    130                 135                 140 gat atc atc gag gcc ggt cgc att cct gtg gtc tct acg att gct cca      480
Asp Ile Ile Glu Ala Gly Arg Ile Pro Val Val Ser Thr Ile Ala Pro
145                 150                 155                 160 ggc gaa gac ggc cag att tac aac att aac gcc gat acc gca gca ggt      528
Gly Glu Asp Gly Gln Ile Tyr Asn Ile Asn Ala Asp Thr Ala Ala Gly
                165                 170                 175 gct ttg gct gca gcg att ggt gca gaa cgc ctg ctg gtt ctc acc aat      576
Ala Leu Ala Ala Ala Ile Gly Ala Glu Arg Leu Leu Val Leu Thr Asn
            180                 185                 190 gtg gaa ggt ctg tac acc gat tgg cct gat aag agc tca ctg gtg tcc      624
Val Glu Gly Leu Tyr Thr Asp Trp Pro Asp Lys Ser Ser Leu Val Ser
        195                 200                 205 aag atc aag gcc acc gag ctg gag gcc att ctt ccg gga ctt gat tcc      672
Lys Ile Lys Ala Thr Glu Leu Glu Ala Ile Leu Pro Gly Leu Asp Ser
    210                 215                 220 ggc atg att cca aag atg gag tct tgc ttg aac gcg gtg cgt ggg gga      720
Gly Met Ile Pro Lys Met Glu Ser Cys Leu Asn Ala Val Arg Gly Gly
225                 230                 235                 240 gta agc gct gct cat gtc att gac ggc cgc atc gcg cac tcg gtg ttg      768
Val Ser Ala Ala His Val Ile Asp Gly Arg Ile Ala His Ser Val Leu
                245                 250                 255 ctg gag ctt ttg acc atg ggt gga att ggc acg atg gtg ctg ccg gat      816
Leu Glu Leu Leu Thr Met Gly Gly Ile Gly Thr Met Val Leu Pro Asp
            260                 265                 270 gtt ttt gat cgg gag aat tat cct gaa ggc acc gtt ttt aga aaa gac      864
Val Phe Asp Arg Glu Asn Tyr Pro Glu Gly Thr Val Phe Arg Lys Asp
        275                 280                 285 gac aag gat ggg gaa ctg                                              882
Asp Lys Asp Gly Glu Leu
    290
```

<210> SEQ ID NO 5
<211> LENGTH: 294
<212> TYPE: PRT
<213> ORGANISM: Corynebacterium glutamicum

<400> SEQUENCE: 5

```
Leu Gln His Phe Arg Asp Lys Ile Val Val Lys Tyr Gly Gly Asn
  1               5                  10                  15

Ala Met Val Asp Asp Leu Lys Ala Leu Phe Ala Ala Asp Met Val
                 20                  25                  30

Phe Leu Arg Thr Val Gly Ala Lys Pro Val Val His Gly Gly Gly
             35                  40                  45

Pro Gln Ile Ser Glu Met Leu Asn Arg Val Gly Leu Gln Gly Glu Phe
        50                  55                  60

Lys Gly Gly Phe Arg Val Thr Thr Pro Glu Val Met Asp Ile Val Arg
 65                  70                  75                  80

Met Val Leu Phe Gly Gln Val Gly Arg Asp Leu Val Gly Leu Ile Asn
                 85                  90                  95

Ser His Gly Pro Tyr Ala Val Gly Thr Ser Gly Glu Asp Ala Gly Leu
```

```
                       100                 105                 110
Phe Thr Ala Gln Lys Arg Met Val Asn Ile Asp Gly Val Pro Thr Asp
            115                 120                 125

Ile Gly Leu Val Gly Asp Ile Ile Asn Val Asp Ala Ser Ser Leu Met
        130                 135                 140

Asp Ile Ile Glu Ala Gly Arg Ile Pro Val Val Ser Thr Ile Ala Pro
145                 150                 155                 160

Gly Glu Asp Gly Gln Ile Tyr Asn Ile Asn Ala Asp Thr Ala Ala Gly
                    165                 170                 175

Ala Leu Ala Ala Ala Ile Gly Ala Glu Arg Leu Leu Val Leu Thr Asn
                180                 185                 190

Val Glu Gly Leu Tyr Thr Asp Trp Pro Asp Lys Ser Ser Leu Val Ser
            195                 200                 205

Lys Ile Lys Ala Thr Glu Leu Glu Ala Ile Leu Pro Gly Leu Asp Ser
        210                 215                 220

Gly Met Ile Pro Lys Met Glu Ser Cys Leu Asn Ala Val Arg Gly Gly
225                 230                 235                 240

Val Ser Ala Ala His Val Ile Asp Gly Arg Ile Ala His Ser Val Leu
                    245                 250                 255

Leu Glu Leu Leu Thr Met Gly Gly Ile Gly Thr Met Val Leu Pro Asp
                260                 265                 270

Val Phe Asp Arg Glu Asn Tyr Pro Glu Gly Thr Val Phe Arg Lys Asp
            275                 280                 285

Asp Lys Asp Gly Glu Leu
        290

<210> SEQ ID NO 6
<211> LENGTH: 882
<212> TYPE: DNA
<213> ORGANISM: Corynebacterium glutamicum

<400> SEQUENCE: 6 ttg cag cac ttc cgc gac aag att gtt gtc gtg aaa tat ggc gga aac     48
Leu Gln His Phe Arg Asp Lys Ile Val Val Val Lys Tyr Gly Gly Asn
 1               5                  10                  15 gcc atg gtg gat gat gat ctc aag gct ctg ttt gct gcc gac atg gtc     96
Ala Met Val Asp Asp Asp Leu Lys Ala Leu Phe Ala Ala Asp Met Val
                20                  25                  30 ttc ttg cgc acc gtg ggc gca aaa cca gtg gtg gtg cac ggt ggt gga    144
Phe Leu Arg Thr Val Gly Ala Lys Pro Val Val Val His Gly Gly Gly
            35                  40                  45 cct cag att tct gag atg cta aac cgt gtg ggt ctc cag ggc gag ttc    192
Pro Gln Ile Ser Glu Met Leu Asn Arg Val Gly Leu Gln Gly Glu Phe
        50                  55                  60 aag ggt ggt ttc cgt gtg acc act cct gag gtc atg gac att gtg cgc    240
Lys Gly Gly Phe Arg Val Thr Thr Pro Glu Val Met Asp Ile Val Arg
65                  70                  75                  80 atg gtg ctc ttt ggt cag gtc ggt cgc gat tta gtt ggt ttg atc aac    288
Met Val Leu Phe Gly Gln Val Gly Arg Asp Leu Val Gly Leu Ile Asn
                85                  90                  95 tct cat ggc cct tac gct gtg gga acc tcc ggt gag gat gcc ggc ctg    336
Ser His Gly Pro Tyr Ala Val Gly Thr Ser Gly Glu Asp Ala Gly Leu
            100                 105                 110 ttt acc gcg cag aag cgc atg gtc aac atc gat ggc gta ccc act gat    384
Phe Thr Ala Gln Lys Arg Met Val Asn Ile Asp Gly Val Pro Thr Asp
        115                 120                 125 att ggt ttg gtc gga gac atc att aat gtc gat gcc tct tcc ttg atg    432
```

```
Ile Gly Leu Val Gly Asp Ile Ile Asn Val Asp Ala Ser Ser Leu Met
    130                 135                 140 gat atc atc gag gcc ggt cgc att cct gtg gtc tct acg att gct cca        480
Asp Ile Ile Glu Ala Gly Arg Ile Pro Val Val Ser Thr Ile Ala Pro
145                 150                 155                 160 ggc gaa gac ggc cag att tac aac att aac gcc gat acc gca gca ggt        528
Gly Glu Asp Gly Gln Ile Tyr Asn Ile Asn Ala Asp Thr Ala Ala Gly
                165                 170                 175 gct ttg gct gca gcg att ggt gca gaa cgc ctg ctg gtt ctc acc aat        576
Ala Leu Ala Ala Ala Ile Gly Ala Glu Arg Leu Leu Val Leu Thr Asn
            180                 185                 190 gtg gaa ggt ctg tac acc gat tgg cct gat aag agc tca ctg gtg tcc        624
Val Glu Gly Leu Tyr Thr Asp Trp Pro Asp Lys Ser Ser Leu Val Ser
        195                 200                 205 aag atc aag gcc acc gag ctg gag gcc att ctt ccg gga ctt gat tcc        672
Lys Ile Lys Ala Thr Glu Leu Glu Ala Ile Leu Pro Gly Leu Asp Ser
    210                 215                 220 ggc atg att cca aag atg gag tct tgc ttg aac gcg gtg cgt ggg gga        720
Gly Met Ile Pro Lys Met Glu Ser Cys Leu Asn Ala Val Arg Gly Gly
225                 230                 235                 240 gta agc gct gct cat gtc att gac ggc cgc atc gcg cac tcg gtg ttg        768
Val Ser Ala Ala His Val Ile Asp Gly Arg Ile Ala His Ser Val Leu
                245                 250                 255 ctg gag ctt ttg acc atg ggt gga att ggc acg atg gtg ctg ccg gat        816
Leu Glu Leu Leu Thr Met Gly Gly Ile Gly Thr Met Val Leu Pro Asp
            260                 265                 270 gtt ttt gat cgg gag aat tat cct gaa ggc acc gtt ttt aga aaa gac        864
Val Phe Asp Arg Glu Asn Tyr Pro Glu Gly Thr Val Phe Arg Lys Asp
        275                 280                 285 gac aag gat ggg gaa ctg                                                 882
Asp Lys Asp Gly Glu Leu
    290

<210> SEQ ID NO 7
<211> LENGTH: 294
<212> TYPE: PRT
<213> ORGANISM: Corynebacterium glutamicum

<400> SEQUENCE: 7

Leu Gln His Phe Arg Asp Lys Ile Val Val Lys Tyr Gly Gly Asn
  1               5                  10                  15

Ala Met Val Asp Asp Asp Leu Lys Ala Ile Phe Ala Ala Asp Met Val
                20                  25                  30

Phe Leu Arg Thr Val Gly Ala Lys Pro Val Val His Gly Gly Gly
            35                  40                  45

Pro Gln Ile Ser Glu Met Leu Asn Arg Val Gly Leu Gln Gly Glu Phe
        50                  55                  60

Lys Gly Gly Phe Arg Val Thr Thr Pro Glu Val Met Asp Ile Val Arg
 65                  70                  75                  80

Met Val Leu Phe Gly Gln Val Gly Arg Asp Leu Val Gly Leu Ile Asn
                85                  90                  95

Ser His Gly Pro Tyr Ala Val Gly Thr Ser Gly Glu Asp Ala Gly Leu
            100                 105                 110

Phe Thr Ala Gln Lys Arg Met Val Asn Ile Asp Gly Val Pro Thr Asp
        115                 120                 125

Ile Gly Leu Val Gly Asp Ile Ile Asn Val Asp Ala Ser Ser Leu Met
    130                 135                 140

Asp Ile Ile Glu Ala Gly Arg Ile Pro Val Val Ser Thr Ile Ala Pro
```

```
                145                 150                 155                 160
Gly Glu Asp Gly Gln Ile Tyr Asn Ile Asn Ala Asp Thr Ala Ala Gly
                165                 170                 175

Ala Leu Ala Ala Ala Ile Gly Ala Glu Arg Leu Leu Val Leu Thr Asn
            180                 185                 190

Val Glu Gly Leu Tyr Thr Asp Trp Pro Asp Lys Ser Ser Leu Val Ser
        195                 200                 205

Lys Ile Lys Ala Thr Glu Leu Glu Ala Ile Leu Pro Gly Leu Asp Ser
    210                 215                 220

Gly Met Ile Pro Lys Met Glu Ser Cys Leu Asn Ala Val Arg Gly Gly
225                 230                 235                 240

Val Ser Ala Ala His Val Ile Asp Gly Arg Ile Ala His Ser Val Leu
                245                 250                 255

Leu Glu Leu Leu Thr Met Gly Gly Ile Gly Thr Met Val Leu Pro Asp
            260                 265                 270

Val Phe Asp Arg Glu Asn Tyr Pro Glu Gly Thr Val Phe Arg Lys Asp
        275                 280                 285

Asp Lys Asp Gly Glu Leu
    290

<210> SEQ ID NO 8
<211> LENGTH: 882
<212> TYPE: DNA
<213> ORGANISM: Corynebacterium glutamicum

<400> SEQUENCE: 8 ttg cag cac ttc cgc gac aag att gtt gtc gtg aaa tat ggc gga aac      48
Leu Gln His Phe Arg Asp Lys Ile Val Val Val Lys Tyr Gly Gly Asn
  1               5                  10                  15 gcc atg gtg gat gat gat ctc aag gct atc ttt gct gcc gac atg gtc      96
Ala Met Val Asp Asp Asp Leu Lys Ala Ile Phe Ala Ala Asp Met Val
             20                  25                  30 ttc ttg cgc acc gtg ggc gca aaa cca gtg gtg gtg cac ggt ggt gga     144
Phe Leu Arg Thr Val Gly Ala Lys Pro Val Val Val His Gly Gly Gly
         35                  40                  45 cct cag att tct gag atg cta aac cgt gtg ggt ctc cag ggc gag ttc     192
Pro Gln Ile Ser Glu Met Leu Asn Arg Val Gly Leu Gln Gly Glu Phe
     50                  55                  60 aag ggt ggt ttc cgt gtg acc act cct gag gtc atg gac att gtg cgc     240
Lys Gly Gly Phe Arg Val Thr Thr Pro Glu Val Met Asp Ile Val Arg
 65                  70                  75                  80 atg gtg ctc ttt ggt cag gtc ggt cgc gat tta gtt ggt ttg atc aac     288
Met Val Leu Phe Gly Gln Val Gly Arg Asp Leu Val Gly Leu Ile Asn
                 85                  90                  95 tct cat ggc cct tac gct gtg gga acc tcc ggt gag gat gcc ggc ctg     336
Ser His Gly Pro Tyr Ala Val Gly Thr Ser Gly Glu Asp Ala Gly Leu
            100                 105                 110 ttt acc gcg cag aag cgc atg gtc aac atc gat ggc gta ccc act gat     384
Phe Thr Ala Gln Lys Arg Met Val Asn Ile Asp Gly Val Pro Thr Asp
        115                 120                 125 att ggt ttg gtc gga gac atc att aat gtc gat gcc tct tcc ttg atg     432
Ile Gly Leu Val Gly Asp Ile Ile Asn Val Asp Ala Ser Ser Leu Met
    130                 135                 140 gat atc atc gag gcc ggt cgc att cct gtg gtc tct acg att gct cca     480
Asp Ile Ile Glu Ala Gly Arg Ile Pro Val Val Ser Thr Ile Ala Pro
145                 150                 155                 160 ggc gaa gac ggc cag att tac aac att aac gcc gat acc gca gca ggt     528
Gly Glu Asp Gly Gln Ile Tyr Asn Ile Asn Ala Asp Thr Ala Ala Gly
```

-continued

```
                    165                 170                 175
gct ttg gct gca gcg att ggt gca gaa cgc ctg ctg gtt ctc acc aat    576
Ala Leu Ala Ala Ala Ile Gly Ala Glu Arg Leu Leu Val Leu Thr Asn
            180                 185                 190 gtg gaa ggt ctg tac acc gat tgg cct gat aag agc tca ctg gtg tcc    624
Val Glu Gly Leu Tyr Thr Asp Trp Pro Asp Lys Ser Ser Leu Val Ser
        195                 200                 205 aag atc aag gcc acc gag ctg gag gcc att ctt ccg gga ctt gat tcc    672
Lys Ile Lys Ala Thr Glu Leu Glu Ala Ile Leu Pro Gly Leu Asp Ser
    210                 215                 220 ggc atg att cca aag atg gag tct tgc ttg aac gcg gtg cgt ggg gga    720
Gly Met Ile Pro Lys Met Glu Ser Cys Leu Asn Ala Val Arg Gly Gly
225                 230                 235                 240 gta agc gct gct cat gtc att gac ggc cgc atc gcg cac tcg gtg ttg    768
Val Ser Ala Ala His Val Ile Asp Gly Arg Ile Ala His Ser Val Leu
                245                 250                 255 ctg gag ctt ttg acc atg ggt gga att ggc acg atg gtg ctg ccg gat    816
Leu Glu Leu Leu Thr Met Gly Gly Ile Gly Thr Met Val Leu Pro Asp
            260                 265                 270 gtt ttt gat cgg gag aat tat cct gaa ggc acc gtt ttt aga aaa gac    864
Val Phe Asp Arg Glu Asn Tyr Pro Glu Gly Thr Val Phe Arg Lys Asp
        275                 280                 285 gac aag gat ggg gaa ctg                                             882
Asp Lys Asp Gly Glu Leu
    290

<210> SEQ ID NO 9
<211> LENGTH: 294
<212> TYPE: PRT
<213> ORGANISM: Corynebacterium glutamicum

<400> SEQUENCE: 9

Leu Gln His Phe Arg Asp Lys Ile Val Val Lys Tyr Gly Gly Asn
1               5                   10                  15

Ala Met Val Asp Asp Leu Lys Ala Ala Phe Ala Ala Asp Val Val
            20                  25                  30

Phe Leu Arg Thr Val Gly Ala Lys Pro Val Val His Gly Gly Gly
        35                  40                  45

Pro Gln Ile Ser Glu Met Leu Asn Arg Val Gly Leu Gln Gly Glu Phe
    50                  55                  60

Lys Gly Gly Phe Arg Val Thr Thr Pro Glu Val Met Asp Ile Val Arg
65                  70                  75                  80

Met Val Leu Phe Gly Gln Val Gly Arg Asp Leu Val Gly Leu Ile Asn
                85                  90                  95

Ser His Gly Pro Tyr Ala Val Gly Thr Ser Gly Glu Asp Ala Gly Leu
            100                 105                 110

Phe Thr Ala Gln Lys Arg Met Val Asn Ile Asp Gly Val Pro Thr Asp
        115                 120                 125

Ile Gly Leu Val Gly Asp Ile Ile Asn Val Asp Ala Ser Ser Leu Met
    130                 135                 140

Asp Ile Ile Glu Ala Gly Arg Ile Pro Val Val Ser Thr Ile Ala Pro
145                 150                 155                 160

Gly Glu Asp Gly Gln Ile Tyr Asn Ile Asn Ala Asp Thr Ala Ala Gly
                165                 170                 175

Ala Leu Ala Ala Ala Ile Gly Ala Glu Arg Leu Leu Val Leu Thr Asn
            180                 185                 190

Val Glu Gly Leu Tyr Thr Asp Trp Pro Asp Lys Ser Ser Leu Val Ser
```

-continued

```
                195                 200                 205
Lys Ile Lys Ala Thr Glu Leu Glu Ala Ile Leu Pro Gly Leu Asp Ser
    210                 215                 220

Gly Met Ile Pro Lys Met Glu Ser Cys Leu Asn Ala Val Arg Gly Gly
225                 230                 235                 240

Val Ser Ala Ala His Val Ile Asp Gly Arg Ile Ala His Ser Val Leu
                245                 250                 255

Leu Glu Leu Leu Thr Met Gly Gly Ile Gly Thr Met Val Leu Pro Asp
            260                 265                 270

Val Phe Asp Arg Glu Asn Tyr Pro Glu Gly Thr Val Phe Arg Lys Asp
                275                 280                 285

Asp Lys Asp Gly Glu Leu
        290
```

<210> SEQ ID NO 10
<211> LENGTH: 882
<212> TYPE: DNA
<213> ORGANISM: Corynebacterium glutamicum

<400> SEQUENCE: 10

```
ttg cag cac ttc cgc gac aag att gtt gtc gtg aaa tat ggc gga aac    48
Leu Gln His Phe Arg Asp Lys Ile Val Val Val Lys Tyr Gly Gly Asn
1               5                   10                  15 gcc atg gtg gat gat gat ctc aag gct gct ttt gct gcc gac gtg gtc    96
Ala Met Val Asp Asp Asp Leu Lys Ala Ala Phe Ala Ala Asp Val Val
            20                  25                  30 ttc ttg cgc acc gtg ggc gca aaa cca gtg gtg gtg cac ggt ggt gga   144
Phe Leu Arg Thr Val Gly Ala Lys Pro Val Val Val His Gly Gly Gly
        35                  40                  45 cct cag att tct gag atg cta aac cgt gtg ggt ctc cag ggc gag ttc   192
Pro Gln Ile Ser Glu Met Leu Asn Arg Val Gly Leu Gln Gly Glu Phe
    50                  55                  60 aag ggt ggt ttc cgt gtg acc act cct gag gtc atg gac att gtg cgc   240
Lys Gly Gly Phe Arg Val Thr Thr Pro Glu Val Met Asp Ile Val Arg
65                  70                  75                  80 atg gtg ctc ttt ggt cag gtc ggt cgc gat tta gtt ggt ttg atc aac   288
Met Val Leu Phe Gly Gln Val Gly Arg Asp Leu Val Gly Leu Ile Asn
                85                  90                  95 tct cat ggc cct tac gct gtg gga acc tcc ggt gag gat gcc ggc ctg   336
Ser His Gly Pro Tyr Ala Val Gly Thr Ser Gly Glu Asp Ala Gly Leu
            100                 105                 110 ttt acc gcg cag aag cgc atg gtc aac atc gat ggc gta ccc act gat   384
Phe Thr Ala Gln Lys Arg Met Val Asn Ile Asp Gly Val Pro Thr Asp
        115                 120                 125 att ggt ttg gtc gga gac atc att aat gtc gat gcc tct tcc ttg atg   432
Ile Gly Leu Val Gly Asp Ile Ile Asn Val Asp Ala Ser Ser Leu Met
    130                 135                 140 gat atc atc gag gcc ggt cgc att cct gtg gtc tct acg att gct cca   480
Asp Ile Ile Glu Ala Gly Arg Ile Pro Val Val Ser Thr Ile Ala Pro
145                 150                 155                 160 ggc gaa gac ggc cag att tac aac att aac gcc gat acc gca gca ggt   528
Gly Glu Asp Gly Gln Ile Tyr Asn Ile Asn Ala Asp Thr Ala Ala Gly
                165                 170                 175 gct ttg gct gca gcg att ggt gca gaa cgc ctg ctg gtt ctc acc aat   576
Ala Leu Ala Ala Ala Ile Gly Ala Glu Arg Leu Leu Val Leu Thr Asn
            180                 185                 190 gtg gaa ggt ctg tac acc gat tgg cct gat aag agc tca ctg gtg tcc   624
Val Glu Gly Leu Tyr Thr Asp Trp Pro Asp Lys Ser Ser Leu Val Ser
        195                 200                 205
```

```
aag atc aag gcc acc gag ctg gag gcc att ctt ccg gga ctt gat tcc         672
Lys Ile Lys Ala Thr Glu Leu Glu Ala Ile Leu Pro Gly Leu Asp Ser
    210                 215                 220 ggc atg att cca aag atg gag tct tgc ttg aac gcg gtg cgt ggg gga         720
Gly Met Ile Pro Lys Met Glu Ser Cys Leu Asn Ala Val Arg Gly Gly
225                 230                 235                 240 gta agc gct gct cat gtc att gac ggc cgc atc gcg cac tcg gtg ttg         768
Val Ser Ala Ala His Val Ile Asp Gly Arg Ile Ala His Ser Val Leu
                245                 250                 255 ctg gag ctt ttg acc atg ggt gga att ggc acg atg gtg ctg ccg gat         816
Leu Glu Leu Leu Thr Met Gly Gly Ile Gly Thr Met Val Leu Pro Asp
            260                 265                 270 gtt ttt gat cgg gag aat tat cct gaa ggc acc gtt ttt aga aaa gac         864
Val Phe Asp Arg Glu Asn Tyr Pro Glu Gly Thr Val Phe Arg Lys Asp
        275                 280                 285 gac aag gat ggg gaa ctg                                                 882
Asp Lys Asp Gly Glu Leu
        290

<210> SEQ ID NO 11
<211> LENGTH: 294
<212> TYPE: PRT
<213> ORGANISM: Corynebacterium glutamicum

<400> SEQUENCE: 11

Leu Gln His Phe Arg Asp Lys Ile Val Val Lys Tyr Gly Gly Asn
 1               5                  10                  15

Ala Met Val Asp Asp Leu Lys Ala Val Phe Ala Ala Asp Val Val
                20                  25                  30

Phe Leu Arg Thr Val Gly Ala Lys Pro Val Val His Gly Gly Gly
            35                  40                  45

Pro Gln Ile Ser Glu Met Leu Asn Arg Val Gly Leu Gln Gly Glu Phe
        50                  55                  60

Lys Gly Gly Phe Arg Val Thr Thr Pro Glu Val Met Asp Ile Val Arg
65                  70                  75                  80

Met Val Leu Phe Gly Gln Val Gly Arg Asp Leu Val Gly Leu Ile Asn
                85                  90                  95

Ser His Gly Pro Tyr Ala Val Gly Thr Ser Gly Glu Asp Ala Gly Leu
            100                 105                 110

Phe Thr Ala Gln Lys Arg Met Val Asn Ile Asp Gly Val Pro Thr Asp
        115                 120                 125

Ile Gly Leu Val Gly Asp Ile Ile Asn Val Asp Ala Ser Ser Leu Met
    130                 135                 140

Asp Ile Ile Glu Ala Gly Arg Ile Pro Val Val Ser Thr Ile Ala Pro
145                 150                 155                 160

Gly Glu Asp Gly Gln Ile Tyr Asn Ile Asn Ala Asp Thr Ala Ala Gly
                165                 170                 175

Ala Leu Ala Ala Ala Ile Gly Ala Glu Arg Leu Leu Val Leu Thr Asn
            180                 185                 190

Val Glu Gly Leu Tyr Thr Asp Trp Pro Asp Lys Ser Ser Leu Val Ser
        195                 200                 205

Lys Ile Lys Ala Thr Glu Leu Glu Ala Ile Leu Pro Gly Leu Asp Ser
    210                 215                 220

Gly Met Ile Pro Lys Met Glu Ser Cys Leu Asn Ala Val Arg Gly Gly
225                 230                 235                 240

Val Ser Ala Ala His Val Ile Asp Gly Arg Ile Ala His Ser Val Leu
```

```
                    245                 250                 255
Leu Glu Leu Leu Thr Met Gly Gly Ile Gly Thr Met Val Leu Pro Asp
            260                 265                 270

Val Phe Asp Arg Glu Asn Tyr Pro Glu Gly Thr Val Phe Arg Lys Asp
        275                 280                 285

Asp Lys Asp Gly Glu Leu
    290

<210> SEQ ID NO 12
<211> LENGTH: 882
<212> TYPE: DNA
<213> ORGANISM: Corynebacterium glutamicum

<400> SEQUENCE: 12 ttg cag cac ttc cgc gac aag att gtt gtc gtg aaa tat ggc gga aac     48
Leu Gln His Phe Arg Asp Lys Ile Val Val Val Lys Tyr Gly Gly Asn
  1               5                  10                  15 gcc atg gtg gat gat gat ctc aag gct gtt ttt gct gcc gac gtg gtc     96
Ala Met Val Asp Asp Asp Leu Lys Ala Val Phe Ala Ala Asp Val Val
             20                  25                  30 ttc ttg cgc acc gtg ggc gca aaa cca gtg gtg gtg cac ggt ggt gga    144
Phe Leu Arg Thr Val Gly Ala Lys Pro Val Val Val His Gly Gly Gly
         35                  40                  45 cct cag att tct gag atg cta aac cgt gtg ggt ctc cag ggc gag ttc    192
Pro Gln Ile Ser Glu Met Leu Asn Arg Val Gly Leu Gln Gly Glu Phe
     50                  55                  60 aag ggt ggt ttc cgt gtg acc act cct gag gtc atg gac att gtg cgc    240
Lys Gly Gly Phe Arg Val Thr Thr Pro Glu Val Met Asp Ile Val Arg
 65                  70                  75                  80 atg gtg ctc ttt ggt cag gtc ggt cgc gat tta gtt ggt ttg atc aac    288
Met Val Leu Phe Gly Gln Val Gly Arg Asp Leu Val Gly Leu Ile Asn
                 85                  90                  95 tct cat ggc cct tac gct gtg gga acc tcc ggt gag gat gcc ggc ctg    336
Ser His Gly Pro Tyr Ala Val Gly Thr Ser Gly Glu Asp Ala Gly Leu
            100                 105                 110 ttt acc gcg cag aag cgc atg gtc aac atc gat ggc gta ccc act gat    384
Phe Thr Ala Gln Lys Arg Met Val Asn Ile Asp Gly Val Pro Thr Asp
        115                 120                 125 att ggt ttg gtc gga gac atc att aat gtc gat gcc tct tcc ttg atg    432
Ile Gly Leu Val Gly Asp Ile Ile Asn Val Asp Ala Ser Ser Leu Met
    130                 135                 140 gat atc atc gag gcc ggt cgc att cct gtg gtc tct acg att gct cca    480
Asp Ile Ile Glu Ala Gly Arg Ile Pro Val Val Ser Thr Ile Ala Pro
145                 150                 155                 160 ggc gaa gac ggc cag att tac aac att aac gcc gat acc gca gca ggt    528
Gly Glu Asp Gly Gln Ile Tyr Asn Ile Asn Ala Asp Thr Ala Ala Gly
                165                 170                 175 gct ttg gct gca gcg att ggt gca gaa cgc ctg ctg gtt ctc acc aat    576
Ala Leu Ala Ala Ala Ile Gly Ala Glu Arg Leu Leu Val Leu Thr Asn
            180                 185                 190 gtg gaa ggt ctg tac acc gat tgg cct gat aag agc tca ctg gtg tcc    624
Val Glu Gly Leu Tyr Thr Asp Trp Pro Asp Lys Ser Ser Leu Val Ser
        195                 200                 205 aag atc aag gcc acc gag ctg gag gcc att ctt ccg gga ctt gat tcc    672
Lys Ile Lys Ala Thr Glu Leu Glu Ala Ile Leu Pro Gly Leu Asp Ser
    210                 215                 220 ggc atg att cca aag atg gag tct tgc ttg aac gcg gtg cgt ggg gga    720
Gly Met Ile Pro Lys Met Glu Ser Cys Leu Asn Ala Val Arg Gly Gly
225                 230                 235                 240
```

```
gta agc gct gct cat gtc att gac ggc cgc atc gcg cac tcg gtg ttg      768
Val Ser Ala Ala His Val Ile Asp Gly Arg Ile Ala His Ser Val Leu
            245                 250                 255 ctg gag ctt ttg acc atg ggt gga att ggc acg atg gtg ctg ccg gat      816
Leu Glu Leu Leu Thr Met Gly Gly Ile Gly Thr Met Val Leu Pro Asp
        260                 265                 270 gtt ttt gat cgg gag aat tat cct gaa ggc acc gtt ttt aga aaa gac      864
Val Phe Asp Arg Glu Asn Tyr Pro Glu Gly Thr Val Phe Arg Lys Asp
    275                 280                 285 gac aag gat ggg gaa ctg                                              882
Asp Lys Asp Gly Glu Leu
    290

<210> SEQ ID NO 13
<211> LENGTH: 20
<212> TYPE: DNA
<213> ORGANISM: Artificial Sequence
<220> FEATURE:
<223> OTHER INFORMATION: Synthetic DNA

<400> SEQUENCE: 13
aatgcggctc gcactgttgc                                                20

<210> SEQ ID NO 14
<211> LENGTH: 21
<212> TYPE: DNA
<213> ORGANISM: Artificial Sequence
<220> FEATURE:
<223> OTHER INFORMATION: Synthetic DNA

<400> SEQUENCE: 14
atcggtgtac agaccttcca c                                              21

<210> SEQ ID NO 15
<211> LENGTH: 22
<212> TYPE: DNA
<213> ORGANISM: Artificial Sequence
<220> FEATURE:
<223> OTHER INFORMATION: Synthetic DNA

<400> SEQUENCE: 15
tcggcagcaa aaacagcctt ga                                             22

<210> SEQ ID NO 16
<211> LENGTH: 23
<212> TYPE: DNA
<213> ORGANISM: Artificial Sequence
<220> FEATURE:
<223> OTHER INFORMATION: Synthetic DNA

<400> SEQUENCE: 16
atctcaaggc tgtttttgct gcc                                            23

<210> SEQ ID NO 17
<211> LENGTH: 20
<212> TYPE: DNA
<213> ORGANISM: Artificial Sequence
<220> FEATURE:
<223> OTHER INFORMATION: Synthetic DNA

<400> SEQUENCE: 17
caagaagacc acgtcggcag                                                20

<210> SEQ ID NO 18
<211> LENGTH: 21
```

```
<212> TYPE: DNA
<213> ORGANISM: Artificial Sequence
<220> FEATURE:
<223> OTHER INFORMATION: Synthetic DNA

<400> SEQUENCE: 18
tttgctgccg acgtggtctt c                                              21

<210> SEQ ID NO 19
<211> LENGTH: 1440
<212> TYPE: DNA
<213> ORGANISM: Corynebacterium glutamicum
<220> FEATURE:
<221> NAME/KEY: CDS
<222> LOCATION: (548)..(1060)

<400> SEQUENCE: 19
tgatctgcag actatcgtgg aaaacctcag ccctgaagaa ggcccagcag gccttaaggg      60
taagaaggct gtgtacctgg gcgatggcga caacaacatg ccaactcct acatgattgg     120 ctttgccacc gcgggcatgg atatttccat catcgctcct gaagggttcc agcctcgtgc    180
ggaattcgtg gagcgcgcgg aaaagcgtgg ccaggaaacc ggcgcgaagg ttgttgtcac    240
cgacagcctc gacgaggttg ccggcgccga tgttgtcatc accgatacct gggtatccat    300
gggtatggaa aacgacggca tcgatcgcac acacctttc gttccttacc aggtcaacga    360
tgaggtcatg gcgaaagcta acgacggcgc catcttcctg cactgccttc ctgcctaccg    420
tggcaaagaa gtggcagcct ccgtgattga tggaccagcg tccaaagttt tcgatgaagc    480
agaaaaccgc ctccacgctc agaaagcact gctggtgtgg ctgctggcca accagccgag    540 gtaagac atg tcc ctt ggc tca acc ccg tca aca ccg gaa aac tta aat        589
        Met Ser Leu Gly Ser Thr Pro Ser Thr Pro Glu Asn Leu Asn
        1               5                   10 ccc gtg act cgc act gca cgc caa gct ctc att ttg cag att ttg gac        637
Pro Val Thr Arg Thr Ala Arg Gln Ala Leu Ile Leu Gln Ile Leu Asp
15                  20                  25                  30 aaa caa aaa gtc acc agc cag gta caa ctg tct gaa ttg ctg ctg gat        685
Lys Gln Lys Val Thr Ser Gln Val Gln Leu Ser Glu Leu Leu Leu Asp
                35                  40                  45 gaa ggc atc gat atc acc cag gcc acc ttg tcc cga gat ctc gat gaa        733
Glu Gly Ile Asp Ile Thr Gln Ala Thr Leu Ser Arg Asp Leu Asp Glu
            50                  55                  60 ctc ggt gca cgc aag gtt cgc ccc gat ggg gga cgc gcc tac tac gcg        781
Leu Gly Ala Arg Lys Val Arg Pro Asp Gly Gly Arg Ala Tyr Tyr Ala
        65                  70                  75 gtc ggc cca gta gat agc atc gcc cgc gaa gat ctc cgg ggt ccg tcg        829
Val Gly Pro Val Asp Ser Ile Ala Arg Glu Asp Leu Arg Gly Pro Ser
    80                  85                  90 gag aag ctg cgc cgc atg ctt gat gaa ctg ctg gtt tct aca gat cat        877
Glu Lys Leu Arg Arg Met Leu Asp Glu Leu Leu Val Ser Thr Asp His
95                  100                 105                 110 tcc ggc aac atc gcg atg ctg cgc acc ccg ccg gga gct gcc cag tac        925
Ser Gly Asn Ile Ala Met Leu Arg Thr Pro Pro Gly Ala Ala Gln Tyr
                115                 120                 125 ctg gca agt ttc atc gat agg gtg ggg ctg aaa gaa gtc gtt ggc acc        973
Leu Ala Ser Phe Ile Asp Arg Val Gly Leu Lys Glu Val Val Gly Thr
            130                 135                 140 atc gct ggt gat gac acc gtt ttc gtt ctc gcc cgt gat ccg ctc aca       1021
Ile Ala Gly Asp Asp Thr Val Phe Val Leu Ala Arg Asp Pro Leu Thr
        145                 150                 155 ggt aaa gaa cta ggt gaa tta ctc agc ggg cgc acc act taaagcgccc       1070
Gly Lys Glu Leu Gly Glu Leu Leu Ser Gly Arg Thr Thr
```

```
Gly Lys Glu Leu Gly Glu Leu Leu Ser Gly Arg Thr Thr
    160                 165                 170 ctagttcaag gcttgttaat cgcttgttaa tgcaggcagg taaggtataa cccgagtgtt    1130
ttttcgagaa ataccaaccc tttcaacaca ataattttct ttaaacatcc ttgctgtcca    1190
ccacggctgg caaggaactt aaaatgaagg agcacacctc atgactaacc gcatcgttct    1250
tgcatactcc ggcggtctgg acaccactgt ggcaattcca tacctgaaga agatgattga    1310
tggtgaagtc atcgcagttt ccctcgacct gggccagggt ggagagaaca tggacaacgt    1370
tcgccagcgt gcattggatg ccggtgcagc tgagtccatc gttgttgatg caaaggatga    1430
gttcgctgag                                                           1440

<210> SEQ ID NO 20
<211> LENGTH: 20
<212> TYPE: DNA
<213> ORGANISM: Artificial Sequence
<220> FEATURE:
<223> OTHER INFORMATION: Synthetic DNA

<400> SEQUENCE: 20
cccagcaggc cttaagggta                                                  20

<210> SEQ ID NO 21
<211> LENGTH: 20
<212> TYPE: DNA
<213> ORGANISM: Artificial Sequence
<220> FEATURE:
<223> OTHER INFORMATION: Synthetic DNA

<400> SEQUENCE: 21
ctcagcgaac tcatcctttg                                                  20

<210> SEQ ID NO 22
<211> LENGTH: 42
<212> TYPE: DNA
<213> ORGANISM: Artificial Sequence
<220> FEATURE:
<223> OTHER INFORMATION: Synthetic DNA

<400> SEQUENCE: 22
cccatccact aaacttaaac agccaaggga catgtcttac ct                          42

<210> SEQ ID NO 23
<211> LENGTH: 42
<212> TYPE: DNA
<213> ORGANISM: Artificial Sequence
<220> FEATURE:
<223> OTHER INFORMATION: Synthetic DNA

<400> SEQUENCE: 23
tgtttaagtt tagtggatgg ggatagggtg gggctgaaag aa                          42

<210> SEQ ID NO 24
<211> LENGTH: 35
<212> TYPE: DNA
<213> ORGANISM: Artificial Sequence
<220> FEATURE:
<223> OTHER INFORMATION: Synthetic DNA

<400> SEQUENCE: 24
atatatggat cctgttcttg atggttttaa gcacg                                  35

<210> SEQ ID NO 25
```

```
<210> SEQ ID NO 25
<211> LENGTH: 32
<212> TYPE: DNA
<213> ORGANISM: Artificial Sequence
<220> FEATURE:
<223> OTHER INFORMATION: Synthetic DNA

<400> SEQUENCE: 25
atatatggat cctgctatct actgggccga cc                                32

<210> SEQ ID NO 26
<211> LENGTH: 22
<212> TYPE: DNA
<213> ORGANISM: Artificial Sequence
<220> FEATURE:
<223> OTHER INFORMATION: Synthetic DNA

<400> SEQUENCE: 26
tcggcagcaa acagagcctt ga                                           22

<210> SEQ ID NO 27
<211> LENGTH: 23
<212> TYPE: DNA
<213> ORGANISM: Artificial Sequence
<220> FEATURE:
<223> OTHER INFORMATION: Synthetic DNA

<400> SEQUENCE: 27
atctcaaggc tctgtttgct gcc                                          23

<210> SEQ ID NO 28
<211> LENGTH: 22
<212> TYPE: DNA
<213> ORGANISM: Artificial Sequence
<220> FEATURE:
<223> OTHER INFORMATION: Synthetic DNA

<400> SEQUENCE: 28
tcggcagcaa agatagcctt ga                                           22

<210> SEQ ID NO 29
<211> LENGTH: 23
<212> TYPE: DNA
<213> ORGANISM: Artificial Sequence
<220> FEATURE:
<223> OTHER INFORMATION: Synthetic DNA

<400> SEQUENCE: 29
atctcaaggc tatctttgct gcc                                          23

<210> SEQ ID NO 30
<211> LENGTH: 1332
<212> TYPE: DNA
<213> ORGANISM: Corynebacterium glutamicum
<220> FEATURE:
<221> NAME/KEY: CDS
<222> LOCATION: (451)..(1332)

<400> SEQUENCE: 30
aacaacgagc aggcgattaa tgcggctcgc actgttgctc gtgacaattt gttcaagtgc    60
gcaatgtttg gatctgatcc aaactggggt cgcgtgttgg ctgcagtcgg catggctgat   120
gctgatatgg aaccagagaa gatttctgtg ttcttcaatg gtcaagcagt atgccttgat   180
tccactggcg ctcctggtgc tcgtgaggtg gatctttccg gcgctgacat tgatgtccga   240
attgatttgg gcaccagtgg ggaaggccag gcaacagttc gaaccactga cctgagcttc   300
```

-continued

```
tcctacgtgg agatcaactc cgcgtacagc tcttaaaaag aaacagcact ccaactaaca      360
agcagggaaa agggcacagg catgaatgac ttgatcaaag atttaggctc tgaggtgcgc      420
gcaaatgtcc tcgctgaggc gttgccatgg ttg cag cac ttc cgc gac aag att      474
                                 Leu Gln His Phe Arg Asp Lys Ile
                                  1               5 gtt gtc gtg aaa tat ggc gga aac gcc atg gtg gat gat gat ctc aag        522
Val Val Val Lys Tyr Gly Gly Asn Ala Met Val Asp Asp Asp Leu Lys
         10                  15                  20 gct gct ttt gct gcc gac atg gtc ttc ttg cgc acc gtg ggc gca aaa        570
Ala Ala Phe Ala Ala Asp Met Val Phe Leu Arg Thr Val Gly Ala Lys
 25                  30                  35                  40 cca gtg gtg gtg cac ggt ggt gga cct cag att tct gag atg cta aac        618
Pro Val Val Val His Gly Gly Gly Pro Gln Ile Ser Glu Met Leu Asn
                 45                  50                  55 cgt gtg ggt ctc cag ggc gag ttc aag ggt ggt ttc cgt gtg acc act        666
Arg Val Gly Leu Gln Gly Glu Phe Lys Gly Gly Phe Arg Val Thr Thr
             60                  65                  70 cct gag gtc atg gac att gtg cgc atg gtg ctc ttt ggt cag gtc ggt        714
Pro Glu Val Met Asp Ile Val Arg Met Val Leu Phe Gly Gln Val Gly
         75                  80                  85 cgc gat tta gtt ggt ttg atc aac tct cat ggc cct tac gct gtg gga        762
Arg Asp Leu Val Gly Leu Ile Asn Ser His Gly Pro Tyr Ala Val Gly
 90                  95                 100 acc tcc ggt gag gat gcc ggc ctg ttt acc gcg cag aag cgc atg gtc        810
Thr Ser Gly Glu Asp Ala Gly Leu Phe Thr Ala Gln Lys Arg Met Val
105                 110                 115                 120 aac atc gat ggc gta ccc act gat att ggt ttg gtc gga gac atc att        858
Asn Ile Asp Gly Val Pro Thr Asp Ile Gly Leu Val Gly Asp Ile Ile
                125                 130                 135 aat gtc gat gcc tct tcc ttg atg gat atc atc gag gcc ggt cgc att        906
Asn Val Asp Ala Ser Ser Leu Met Asp Ile Ile Glu Ala Gly Arg Ile
            140                 145                 150 cct gtg gtc tct acg att gct cca ggc gaa gac ggc cag att tac aac        954
Pro Val Val Ser Thr Ile Ala Pro Gly Glu Asp Gly Gln Ile Tyr Asn
        155                 160                 165 att aac gcc gat acc gca gca ggt gct ttg gct gca gcg att ggt gca       1002
Ile Asn Ala Asp Thr Ala Ala Gly Ala Leu Ala Ala Ala Ile Gly Ala
170                 175                 180 gaa cgc ctg ctg gtt ctc acc aat gtg gaa ggt ctg tac acc gat tgg       1050
Glu Arg Leu Leu Val Leu Thr Asn Val Glu Gly Leu Tyr Thr Asp Trp
185                 190                 195                 200 cct gat aag agc tca ctg gtg tcc aag atc aag gcc acc gag ctg gag       1098
Pro Asp Lys Ser Ser Leu Val Ser Lys Ile Lys Ala Thr Glu Leu Glu
                205                 210                 215 gcc att ctt ccg gga ctt gat tcc ggc atg att cca aag atg gag tct       1146
Ala Ile Leu Pro Gly Leu Asp Ser Gly Met Ile Pro Lys Met Glu Ser
            220                 225                 230 tgc ttg aac gcg gtg cgt ggg gga gta agc gct gct cat gtc att gac       1194
Cys Leu Asn Ala Val Arg Gly Gly Val Ser Ala Ala His Val Ile Asp
        235                 240                 245 ggc cgc atc gcg cac tcg gtg ttg ctg gag ctt tgg acc atg ggt gga       1242
Gly Arg Ile Ala His Ser Val Leu Leu Glu Leu Trp Thr Met Gly Gly
    250                 255                 260 att ggc acg atg gtg ctg ccg gat gtt ttt gat cgg gag aat tat cct       1290
Ile Gly Thr Met Val Leu Pro Asp Val Phe Asp Arg Glu Asn Tyr Pro
265                 270                 275                 280 gaa ggc acc gtt ttt aga aaa gac gac aag gat ggg gaa ctg                1332
Glu Gly Thr Val Phe Arg Lys Asp Asp Lys Asp Gly Glu Leu
                285                 290
```

```
<210> SEQ ID NO 31
<211> LENGTH: 1440
<212> TYPE: DNA
<213> ORGANISM: Corynebacterium glutamicum
<220> FEATURE:
<221> NAME/KEY: CDS
<222> LOCATION: (170)..(1126)

<400> SEQUENCE: 31
cgcgacgtcg caaagcaagc tgttcttgat ggttttaagc acggcgttat tttgaatgca      60
ccggcggaca acattatccg tttgaccccg ccgctggtga tcaccgacga agaaatcgca     120
gacgcagtca aggctattgc cgagacaatc gcataaagga ctcaaactt atg act tca    178
                                                      Met Thr Ser
                                                        1 caa cca cag gtt cgc cat ttt ctg gct gat gat gat ctc acc cct gca      226
Gln Pro Gln Val Arg His Phe Leu Ala Asp Asp Asp Leu Thr Pro Ala
      5                  10                 15 gag cag gca gag gtt ttg acc cta gcc gca aag ctc aag gca gcg ccg      274
Glu Gln Ala Glu Val Leu Thr Leu Ala Ala Lys Leu Lys Ala Ala Pro
 20                  25                 30                  35 ttt tcg gag cgt cca ctc gag gga cca aag tcc gtt gca gtt ctt ttt     322
Phe Ser Glu Arg Pro Leu Glu Gly Pro Lys Ser Val Ala Val Leu Phe
                 40                 45                  50 gat aag act tca act cgt act cgc ttc tcc ttc gac gcg ggc atc gct      370
Asp Lys Thr Ser Thr Arg Thr Arg Phe Ser Phe Asp Ala Gly Ile Ala
             55                 60                  65 cat ttg ggt gga cac gcc atc gtc gtg gat tcc ggt agc tca cag atg      418
His Leu Gly Gly His Ala Ile Val Val Asp Ser Gly Ser Ser Gln Met
     70                 75                  80 ggt aag ggc gag tcc ctg cag gac acc gca gct gta ttg tcc cgc tac      466
Gly Lys Gly Glu Ser Leu Gln Asp Thr Ala Ala Val Leu Ser Arg Tyr
 85                  90                 95 gtg gaa gca att gtg tgg cgc acc tac gca cac agc aat ttc cac gcc      514
Val Glu Ala Ile Val Trp Arg Thr Tyr Ala His Ser Asn Phe His Ala
100                 105                 110                 115 atg gcg gag acg tcc act gtg ccg ctg gtg aac tcc ttg tcc gat gat      562
Met Ala Glu Thr Ser Thr Val Pro Leu Val Asn Ser Leu Ser Asp Asp
                120                 125                 130 ctg cac cca tgc cag att ctg gct gat ctg cag act atc gtg gaa aac      610
Leu His Pro Cys Gln Ile Leu Ala Asp Leu Gln Thr Ile Val Glu Asn
            135                 140                 145 ctc agc cct gaa gaa ggc cca gca ggc ctt aag ggt aag aag gct gtg      658
Leu Ser Pro Glu Glu Gly Pro Ala Gly Leu Lys Gly Lys Lys Ala Val
        150                 155                 160 tac ctg ggc gat ggc gac aac aac atg gcc aac tcc tac atg att ggc      706
Tyr Leu Gly Asp Gly Asp Asn Asn Met Ala Asn Ser Tyr Met Ile Gly
    165                 170                 175 ttt gcc acc gcg ggc atg gat att tcc atc atc gct cct gaa ggg ttc      754
Phe Ala Thr Ala Gly Met Asp Ile Ser Ile Ile Ala Pro Glu Gly Phe
180                 185                 190                 195 cag cct cgt gcg gaa ttc gtg gag cgc gcg gaa aag cgt ggc cag gaa      802
Gln Pro Arg Ala Glu Phe Val Glu Arg Ala Glu Lys Arg Gly Gln Glu
                200                 205                 210 acc ggc gcg aag gtt gtt gtc acc gac agc ctc gac gag gtt gcc ggc      850
Thr Gly Ala Lys Val Val Val Thr Asp Ser Leu Asp Glu Val Ala Gly
            215                 220                 225 gcc gat gtt gtc atc acc gat acc tgg gta tcc atg ggt atg gaa aac      898
Ala Asp Val Val Ile Thr Asp Thr Trp Val Ser Met Gly Met Glu Asn
        230                 235                 240
```

-continued

```
gac ggc atc gat cgc acc aca cct ttc gtt cct tac cag gtc aac gat       946
Asp Gly Ile Asp Arg Thr Thr Pro Phe Val Pro Tyr Gln Val Asn Asp
    245                 250                 255 gag gtc atg gcg aaa gct aac gac ggc gcc atc ttc ctg cac tgc ctt       994
Glu Val Met Ala Lys Ala Asn Asp Gly Ala Ile Phe Leu His Cys Leu
260                 265                 270                 275 cct gcc tac cgt ggc aaa gaa gtg gca gcc tcc gtg att gat gga cca      1042
Pro Ala Tyr Arg Gly Lys Glu Val Ala Ala Ser Val Ile Asp Gly Pro
                280                 285                 290 gcg tcc aaa gtt ttc gat gaa gca gaa aac cgc ctc cac gct cag aaa      1090
Ala Ser Lys Val Phe Asp Glu Ala Glu Asn Arg Leu His Ala Gln Lys
            295                 300                 305 gca ctg ctg gtg tgg ctg ctg gcc aac cag ccg agg taagacatgt           1136
Ala Leu Leu Val Trp Leu Leu Ala Asn Gln Pro Arg
        310                 315 cccttggctc aacccgtca acaccggaaa acttaaatcc cgtgactcgc actgcacgcc     1196
aagctctcat tttgcagatt tggacaaac aaaaagtcac cagccaggta caactgtctg     1256
aattgctgct ggatgaaggc atcgatatca cccaggccac cttgtcccga gatctcgatg    1316
aactcggtgc acgcaaggtt cgccccgatg ggggacgcgc ctactacgcg gtcggcccag    1376
tagatagcat cgcccgcgaa gatctccggg gtccgtcgga aagctgcgc cgcatgcttg     1436 atga                                                                  1440

<210> SEQ ID NO 32
<211> LENGTH: 1806
<212> TYPE: DNA
<213> ORGANISM: Corynebacterium glutamicum
<220> FEATURE:
<221> NAME/KEY: CDS
<222> LOCATION: (301)..(1503)

<400> SEQUENCE: 32
aagtttcatc gatagggtgg ggctgaaaga agtcgttggc accatcgctg gtgatgacac      60
cgttttcgtt ctcgcccgtg atccgctcac aggtaaagaa ctaggtgaat tactcagcgg     120
gcgcaccact taaagcgccc ctagttcaag gcttgttaat cgcttgttaa tgcaggcagg    180
taaggtataa cccgagtgtt ttttcgagga ataccaaccc tttcaacaca ataattttct     240
ttaaacatcc ttgctgtcca ccacggctgg caaggaactt aaaatgaagg agcacacctc     300 atg act aac cgc atc gtt ctt gca tac tcc ggc ggt ctg gac acc act       348
Met Thr Asn Arg Ile Val Leu Ala Tyr Ser Gly Gly Leu Asp Thr Thr
1               5                   10                  15 gtg gca att cca tac ctg aag aag atg att gat ggt gaa gtc atc gca       396
Val Ala Ile Pro Tyr Leu Lys Lys Met Ile Asp Gly Glu Val Ile Ala
                20                  25                  30 gtt tcc ctc gac ctg ggc cag ggt gga gag aac atg gac aac gtt cgc       444
Val Ser Leu Asp Leu Gly Gln Gly Gly Glu Asn Met Asp Asn Val Arg
            35                  40                  45 cag cgt gca ttg gat gcc ggt gca gct gag tcc atc gtt gtt gat gca       492
Gln Arg Ala Leu Asp Ala Gly Ala Ala Glu Ser Ile Val Val Asp Ala
        50                  55                  60 aag gat gag ttc gct gag gag tac tgc ctg cca acc atc aag gca aac       540
Lys Asp Glu Phe Ala Glu Glu Tyr Cys Leu Pro Thr Ile Lys Ala Asn
65                  70                  75                  80 ggc atg tac atg aag cag tac cca ctg gtt tct gca atc tcc cgc cca       588
Gly Met Tyr Met Lys Gln Tyr Pro Leu Val Ser Ala Ile Ser Arg Pro
                85                  90                  95 ctg atc gtc aag cac ctc gtt gag gct ggc aag cag ttc aac ggt acc       636
```

```
                                                         -continued

Leu Ile Val Lys His Leu Val Glu Ala Gly Lys Gln Phe Asn Gly Thr
            100                 105                 110 cac gtt gca cac ggc tgc act ggt aag ggc aac gac cag gtt cgt ttc       684
His Val Ala His Gly Cys Thr Gly Lys Gly Asn Asp Gln Val Arg Phe
        115                 120                 125 gag gtc ggc ttc atg gac acc gat cca aac ctg gag atc att gca cct       732
Glu Val Gly Phe Met Asp Thr Asp Pro Asn Leu Glu Ile Ile Ala Pro
    130                 135                 140 gct cgt gac ttc gca tgg acc cgc gac aag gct atc gcc ttc gcc gag       780
Ala Arg Asp Phe Ala Trp Thr Arg Asp Lys Ala Ile Ala Phe Ala Glu
145                 150                 155                 160 gag aac aac gtt cca atc gag cag tcc gtg aag tcc cca ttc tcc atc       828
Glu Asn Asn Val Pro Ile Glu Gln Ser Val Lys Ser Pro Phe Ser Ile
                165                 170                 175 gac cag aac gtc tgg ggc cgc gct att gag acc ggt tac ctg gaa gat       876
Asp Gln Asn Val Trp Gly Arg Ala Ile Glu Thr Gly Tyr Leu Glu Asp
            180                 185                 190 ctg tgg aat gct cca acc aag gac atc tac gca tac acc gag gat cca       924
Leu Trp Asn Ala Pro Thr Lys Asp Ile Tyr Ala Tyr Thr Glu Asp Pro
        195                 200                 205 gct ctg ggt aac gct cca gat gag gtc atc atc tcc ttc gag ggt ggc       972
Ala Leu Gly Asn Ala Pro Asp Glu Val Ile Ile Ser Phe Glu Gly Gly
    210                 215                 220 aag cca gtc tcc atc gat ggc cgt cca gtc tcc gta ctg cag gct att      1020
Lys Pro Val Ser Ile Asp Gly Arg Pro Val Ser Val Leu Gln Ala Ile
225                 230                 235                 240 gaa gag ctg aac cgt cgt gca ggc gca cag ggc gtt ggc cgc ctt gac      1068
Glu Glu Leu Asn Arg Arg Ala Gly Ala Gln Gly Val Gly Arg Leu Asp
                245                 250                 255 atg gtt gag gac cgt ctc gtg ggc atc aag tcc cgc gaa atc tac gaa      1116
Met Val Glu Asp Arg Leu Val Gly Ile Lys Ser Arg Glu Ile Tyr Glu
            260                 265                 270 gca cca ggc gca atc gca ctg att aag gct cac gag gct ttg gaa gat      1164
Ala Pro Gly Ala Ile Ala Leu Ile Lys Ala His Glu Ala Leu Glu Asp
        275                 280                 285 gtc acc atc gag cgc gaa ctg gct cgc tac aag cgc ggc gtt gac gca      1212
Val Thr Ile Glu Arg Glu Leu Ala Arg Tyr Lys Arg Gly Val Asp Ala
    290                 295                 300 cgt tgg gct gag gaa gta tac gac ggc ctg tgg ttc gga cct ctg aag      1260
Arg Trp Ala Glu Glu Val Tyr Asp Gly Leu Trp Phe Gly Pro Leu Lys
305                 310                 315                 320 cgc tcc ctg gac gcg ttc att gat tcc acc cag gag cac gtc acc ggc      1308
Arg Ser Leu Asp Ala Phe Ile Asp Ser Thr Gln Glu His Val Thr Gly
                325                 330                 335 gat atc cgc atg gtt ctg cac gca ggt tcc atc acc atc aat ggt cgt      1356
Asp Ile Arg Met Val Leu His Ala Gly Ser Ile Thr Ile Asn Gly Arg
            340                 345                 350 cgt tcc agc cac tcc ctg tac gac ttc aac ctg gct acc tac gac acc      1404
Arg Ser Ser His Ser Leu Tyr Asp Phe Asn Leu Ala Thr Tyr Asp Thr
        355                 360                 365 ggc gac acc ttc gac cag acc ctg gct aag ggc ttt gtc cag ctg cac      1452
Gly Asp Thr Phe Asp Gln Thr Leu Ala Lys Gly Phe Val Gln Leu His
    370                 375                 380 ggt ctg tcc tcc aag atc gct aac aag cgc gat cgc gaa gct ggc aac      1500
Gly Leu Ser Ser Lys Ile Ala Asn Lys Arg Asp Arg Glu Ala Gly Asn
385                 390                 395                 400 aac taagccacct ttcaagcat ccagactaga acttcaagta tttagaaagt            1553
Asn agaagaacac cacatggaac agcacggaac caatgaaggt gcgctgtggg gcggccgctt    1613
```

```
ctccggtgga ccctccgagg ccatgttcgc cttgagtgtc tccactcatt tcgactgggt    1673
tttggcccct tatgatgtgt tggcctccaa ggcacacgcc aaggttttgc accaagcaga    1733
tctactttct gatgaagatc tagccaccat gctggctggg cttgatcagc tgggcaagga    1793
tgtcgccgac gga                                                       1806
```

PROCESS FOR PRODUCING L-ARGININE, L-ORNITHINE OR L-CITRULLINE

TECHNICAL FIELD

The present invention relates to a process for producing L-arginine, L-ornithine or L-citrulline.

BACKGROUND ART

In microorganisms, L-arginine is biosynthesized from L-glutamic acid through eight reaction steps. L-ornithine and L-citrulline are intermediates on the L-arginine biosynthetic pathway. Biosynthesis of L-arginine, L-ornithine and L-citrulline is regulated similarly to that of other amino acids.

In coryneform bacteria, for example, transcription of an operon composed of genes encoding enzymes responsible for L-arginine biosynthesis (hereinafter abbreviated as arginine operon) is repressed by the arginine repressor (hereinafter referred to as ArgR) (see patent publication No. 1). It is known that in coryneform bacteria N-acetylglutamate kinase, which is the second enzyme on the biosynthetic pathway from L-glutamic acid to L-arginine (EC: 2.7.2.8, hereinafter sometimes abbreviated as ArgB), is subject to feedback inhibition by L-arginine (see non-patent publication No. 2).

L-Arginine, L-ornithine and L-citrulline are produced using microorganisms as well as other amino acids, and studies have been conducted, as in the case of other amino acids, to enhance the productivity of these amino acids by the use of means such as mutation or recombinant DNA techniques.

For example, there is a report that *Corynebacterium glutamicum* K65 (FERM BP-1115) having enhanced arginine productivity was obtained by transforming *Corynebacterium glutamicum* with a DNA fragment containing a gene responsible for arginine biosynthesis and then carrying out mutagenesis (see patent publication No. 2).

*Corynebacterium glutamicum* wherein the repression of arginine biosynthetic enzymes is cancelled (see non-patent publication No. 1) and *Corynebacterium glutamicum* wherein the repression of arginine biosynthetic enzymes is cancelled, feedback inhibition by L-arginine is desensitized and membrane permeability of L-arginine is enhanced (see non-patent publication No. 3) have also been obtained by mutagenesis.

Coryneform bacteria in which DNA encoding ArgR is destroyed (see patent publication No. 1) have been obtained by recombinant DNA techniques.

However, there has been no report so far about what mutation should be introduced into DNA encoding ArgB or ArgR to obtain a strain in which mutations are introduced into both of the DNAs respectively encoding ArgB and ArgR and which has enhanced L-arginine productivity.

Patent publication No. 1:
  Japanese Published Unexamined Patent Application No. 51790/02
Patent publication No. 2:
  Japanese Published Unexamined Patent Application No. 79597/88
Non-patent publication No. 1:
  Agricultural & Biological Chemistry, vol. 43, p. 105-111 (1979)
Non-patent publication No. 2:
  Journal of Bacteriology, vol. 91, p. 617 (1966)
Non-patent publication No. 3:
  Agricultural & Biological Chemistry, vol. 36, p. 1675-1684 (1972)

DISCLOSURE OF THE INVENTION

Problems To Be Solved by the Invention

An object of the present invention is to provide an efficient process for producing L-arginine, L-ornithine or L-citrulline.

Means for Solving the Problems

The present invention relates to the following (1) to (18).
(1) A polypeptide which has:
  (i) an amino acid sequence wherein one or more amino acid residues are substituted in the region at positions 20 to 38 from the N terminus of the amino acid sequence shown in SEQ ID NO: 1; or
  (ii) an amino acid sequence wherein one or more amino acid residues are substituted in the region at positions 20 to 38 from the N terminus of the amino acid sequence shown in SEQ ID NO: 1 and one or more amino acid residues are deleted, substituted or added in the region at positions 1 to 19 or 39 to 294; and which has N-acetylglutamate kinase activity.
(2) A polypeptide which has:
  (i) an amino acid sequence wherein one or more amino acid residues are substituted in the region at positions 26 to 31 from the N terminus of the amino acid sequence shown in SEQ ID NO: 1; or
  (ii) an amino acid sequence wherein one or more amino acid residues are substituted in the region at positions 26 to 31 from the N terminus of the amino acid sequence shown in SEQ ID NO: 1 and one or more amino acid residues are deleted, substituted or added in the region at positions 1 to 25 or 32 to 294; and which has N-acetylglutamate kinase activity.
(3) A polypeptide which has:
  (i) an amino acid sequence wherein the amino acid residue at position 26 or 31 from the N terminus of the amino acid sequence shown in SEQ ID NO: 1 is substituted;
  (ii) an amino acid sequence wherein the amino acid residues at positions 26 and 31 from the N terminus of the amino acid sequence shown in SEQ ID NO: 1 are substituted; or
  (iii) an amino acid sequence wherein one or more amino acid residues other than those at the substituted positions are deleted, substituted or added in the amino acid sequence of the above (i) or (ii); and
  which has N-acetylglutamate kinase activity.
(4) A polypeptide which has:
  (i) an amino acid sequence selected from the group consisting of the amino acid sequences shown in SEQ ID NOS: 3, 5, 7, 9 and 11;
  (ii) an amino acid sequence wherein one or more amino acid residues other than residue 26 are deleted, substituted or added in the amino acid sequence selected from the group consisting of the amino acid sequences shown in SEQ ID NOS: 3, 5 and 7;
  (iii) an amino acid sequence wherein one or more amino acid residues other than residue 31 are deleted, substituted or added in the amino acid sequence shown in SEQ ID NO: 9; or
  (iv) an amino acid sequence wherein one or more amino acid residues other than residues 26 and 31 are deleted, substituted or added in the amino acid sequence shown in SEQ ID NO: 11; and which has N-acetylglutamate kinase activity.
(5) A DNA encoding the polypeptide according to any one of the above (1) to (4).
(6) A DNA having a nucleotide sequence selected from the group consisting of the nucleotide sequences shown in SEQ ID NOS: 4, 6, 8, 10 and 12.
(7) A DNA which hybridizes with DNA consisting of a nucleotide sequence complementary to the nucleotide sequence of DNA encoding a polypeptide having the amino acid sequence shown in SEQ ID NO: 1 under stringent conditions,
which is selected from the group consisting of the following (i) to (iii):
(i) DNA encoding a polypeptide wherein the amino acid residue corresponding to the residue at position 26 from the N terminus of the amino acid sequence shown in SEQ ID NO: 1 is an amino acid residue other than L-alanine;
(ii) DNA encoding a polypeptide wherein the amino acid residue corresponding to the residue at position 31 from the N terminus of the amino acid sequence shown in SEQ ID NO: 1 is an amino acid residue other than L-methionine; and
(iii) DNA encoding a polypeptide wherein the amino acid residue corresponding to the residue at position 26 from the N terminus of the amino acid sequence shown in SEQ ID NO: 1 is an amino acid residue other than L-alanine and the amino acid residue corresponding to the residue at position 31 is an amino acid residue other than L-methionine, and which encodes a polypeptide having N-acetylglutamate kinase activity.
(8) The DNA according to the above (7), wherein the amino acid residue corresponding to the residue at position 26 from the N terminus of the amino acid sequence shown in SEQ ID NO: 1 is L-valine, L-leucine or L-isoleucine and the amino acid residue corresponding to the residue at position 31 is L-valine.
(9) A DNA which hybridizes with DNA consisting of a nucleotide sequence complementary to the nucleotide sequence of DNA encoding a polypeptide having the amino acid sequence shown in SEQ ID NO: 1 under stringent conditions,
which is selected from the group consisting of the following (i) to (iii):
(i) DNA having a nucleotide sequence wherein the region corresponding to the region at positions 76 to 78 from the 5' end of the nucleotide sequence shown in SEQ ID NO: 2 is guanine-thymidine-thymidine, cytosine-thymidine-guanine or adenine-thymidine-cytosine;
(ii) DNA having a nucleotide sequence wherein the region corresponding to the region at positions 91 to 93 from the 5' end of the nucleotide sequence shown in SEQ ID NO: 2 is guanine-thymidine-guanine; and
(iii) DNA having a nucleotide sequence wherein the region corresponding to the region at positions 76 to 78 from the 5' end of the nucleotide sequence shown in SEQ ID NO: 2 is guanine-thymidine-thymidine, cytosine-thymidine-guanine or adenine-thymidine-cytosine, and the region corresponding to the region at positions 91 to 93 is guanine-thymidine-guanine; and
which encodes a polypeptide having N-acetylglutamate kinase activity.
(10) A recombinant DNA which is obtained by incorporating the DNA according to any one of the above (5) to (9) into a vector.
(11) A microorganism which is obtained by introducing the recombinant DNA according to the above (10).
(12) A microorganism having the DNA according to any one of the above (5) to (9).
(13) The microorganism according to the above (11) or (12), wherein the transcriptional repression activity of the arginine repressor on the arginine operon is reduced or lost.
(14) The microorganism according to any one of the above (11) to (13), wherein ornithine carbamoyl transferase activity is reduced or lost.
(15) The microorganism according to any one of the above (11) to (14), wherein argininosuccinate synthase activity is reduced or lost.
(16) The microorganism according to any one of the above (11) to (15), wherein the microorganism is a microorganism belonging to the genus *Corynebacterium*.
(17) The microorganism according to the above (11) to (16), wherein the microorganism is a microorganism belonging to *Corynebacterium glutamicum*.
(18) A process for producing L-arginine, L-ornithine or L-citrulline which comprises culturing the microorganism according to any one of the above (11) to (17) in a medium, allowing L-arginine, L-ornithine or L-citrulline to form and accumulate in the culture, and recovering L-arginine, L-ornithine or L-citrulline from the culture.

Effect Of The Invention

The present invention provides an efficient process for producing L-arginine, L-ornithine or L-citrulline.

BEST MODES FOR CARRYING OUT THE INVENTION

The polypeptides of the present invention include a polypeptide which has an amino acid sequence wherein one or more amino acid residues are substituted in the region at positions 20 to 38 from the N terminus of the amino acid sequence shown in SEQ ID NO: 1 and which has N-acetylglutamate kinase activity (hereinafter referred to as ArgB activity).

The amino acid sequence shown in SEQ ID NO: 1 is the amino acid sequence of ArgB of *Corynebacterium glutamicum* ATCC 13032 and is encoded by DNA having the nucleotide sequence shown in SEQ ID NO: 2. The DNA having the nucleotide sequence shown in SEQ ID NO: 2 is registered as NCgl1342 in DDBJ/GenBank/EMBL.

The region consisting of the amino acid sequence at positions 20 to 38 from the N terminus of the amino acid sequence shown in SEQ ID NO: 1 is assumed to be a region which forms α-helix, judging from the relation between the amino acid sequence of ArgB of *Escherichia coli* and its three-dimensional structure [Structure, 10, 329-342 (2002)] and from the homology of the said amino acid sequence to the amino acid sequence of ArgB of *Corynebacterium glutamicum*.

The amino acid substitution may occur at any site in the region at positions 20 to 38 from the N terminus of the amino acid sequence shown in SEQ ID NO: 1, but the substitution site is preferably in the region at positions 26 to 31.

The number of amino acid residues which are substituted is not specifically limited insofar as a polypeptide having the substituted amino acid sequence has ArgB activity, preferably ArgB activity wherein feedback inhibition by L-arginine is reduced or removed. The suitable number is preferably 1 to 10, more preferably 1 to 5, further preferably 1 or 2.

It can be confirmed that the polypeptide has ArgB activity wherein feedback inhibition by L-arginine is reduced or canceled by checking that its ArgB activity in the presence of L-arginine is higher than that of the polypeptide having the amino acid sequence shown in SEQ ID NO: 1 in the presence of L-arginine. The L-arginine concentration is preferably 5 mmol/l or more, further preferably 10 mmol/l or more.

ArgB activity of a polypeptide can be measured, for example, by methods such as a method in which pyruvic acid formed by the reaction of phosphoenolpyruvic acid-pyruvate kinase system is colorimetrically determined as 2,4-dinitrophenylhydrazone using ATP and N-acetyl-L-glutamic acid as subsrate [Meth. Enzymol., 17, 251-255 (1970)], and a method in which acetylglutamte 5-phosphate which is formed by reacting ATP and N-acetyl-L-glutamic acid with hydroxylamine is determined as hydroxamic acid [Meth. Enzymol., 17, 269-272 (1970)].

The amino acids to be substituted are not specifically limited insofar as a polypeptide having the substituted amino acid sequence has ArgB activity, preferably ArgB activity wherein feedback inhibition by L-arginine is reduced or canceled, and they may be either natural or not.

Examples of the natural amino acids are L-alanine, L-asparagine, L-aspartic acid, L-glutamine, L-glutamic acid, glycine, L-histidine, L-isoleucine, L-leucine, L-lysine, L-arginine, L-methionine, L-phenylalanine, L-proline, L-serine, L-threonine, L-tryptophan, L-tyrosine, L-valine and L-cysteine.

The following are examples of the amino acids capable of mutual substitution. The amino acids in the same group can be mutually substituted.

Group A: leucine, isoleucine, norleucine, valine, norvaline, alanine, 2-aminobutanoic acid, methionine, O-methylserine, t-butylglycine, t-butylalanine, cyclohexylalanine Group B: aspartic acid, glutamic acid, isoaspartic acid, isoglutamic acid, 2-aminoadipic acid, 2-aminosuberic acid Group C: asparagine, glutamine Group D: lysine, arginine, ornithine, 2,4-diaminobutanoic acid, 2,3-diaminopropionic acid Group E: proline, 3-hydroxyproline, 4-hydroxyproline Group F: serine, threonine, homoserine Group G: phenylalanine, tyrosine The polypeptides of the present invention also include a polypeptide which has an amino acid sequence wherein the amino acid residue at position 26 or 31, or both of the amino acid residues at positions 26 and 31 from the N terminus of the amino acid sequence shown in SEQ ID NO: 1 are substituted and which has ArgB activity.

In the polypeptide of the present invention, one or more amino acid residues may be deleted, substituted or added at sites other than the sites which have been substituted in the amino acid sequence insofar as the polypeptide has ArgB activity.

The number of amino acid residues which are deleted, substituted or added is not specifically limited, and the suitable number is 1 to dozens, preferably 1 to 20, more preferably 1 to 10, further preferably 1 to 5.

The amino acid residues to be substituted are the same as the above amino acid residues capable of being substituted in the region at positions 20 to 38 from the N terminus of the amino acid sequence shown in SEQ ID NO: 1.

"Deletion, substitution or addition" refers to deletion, substitution or addition of a single or plural amino acid residues in the same sequence, and they may take place simultaneously.

In order that the polypeptide of the present invention may have ArgB activity, it is desirable that the polypeptide has at least 60% homology, usually 80% or more homology, specifically 95% or more homology to the polypeptide having the amino acid sequence shown in SEQ ID NO: 1.

In the present invention, the homology among amino acid sequences and nucleotide sequences can be determined by using algorithm BLAST by Karlin and Altschul [Proc. Natl. Acad. Sci. USA, 90, 5873 (1993)] and FASTA [Methods Enzymol., 183, 63 (1990)]. On the basis of the algorithm BLAST, programs such as BLASTN and BLASTX have been developed [J. Mol. Biol., 215, 403 (1990)]. When a nucleotide sequence is analyzed by BLASTN on the basis of BLAST, the parameters, for instance, are as follows: score=100 and wordlength=12. When an amino acid sequence is analyzed by BLASTX on the basis of BLAST, the parameters, for instance, are as follows: score=50 and wordlength=3. When BLAST and Gapped BLAST programs are used, default parameters of each program are used. The specific techniques for these analyses are known (http://www.ncbi.nlm.nih.gov.).

More specific examples of the amino acid sequences of the polypeptides of the present invention are: the amino acid sequence shown in SEQ ID NO: 3, in which alanine at position 26 from the N terminus of the amino acid sequence shown in SEQ ID NO: 1 is substituted by valine; the amino acid sequence shown in SEQ ID NO: 5, in which alanine at position 26 from the N terminus of the amino acid sequence shown in SEQ ID NO: 1 is substituted by leucine; the amino acid sequence shown in SEQ ID NO: 7, in which alanine at position 26 from the N terminus of the amino acid sequence shown in SEQ ID NO: 1 is substituted by isoleucine; the amino acid sequence shown in SEQ ID NO: 9, in which methionine at position 31 from the N terminus of the amino acid sequence shown in SEQ ID NO: 1 is substituted by valine; and the amino acid sequence shown in SEQ ID NO: 11, in which alanine at position 26 and methionine at position 31 from the N terminus of the amino acid sequence shown in SEQ ID NO: 1 are respectively substituted by valine.

Examples of the DNAs of the present invention include DNAs encoding the polypeptides of the present invention, specifically, DNAs having the nucleotide sequences shown in SEQ ID NOS: 4, 6, 8, 10 and 12 which encode the polypeptides having the amino acid sequences shown in SEQ ID NOS: 3, 5, 7, 9 and 11, respectively.

The DNAs of the present invention include DNA which hybridizes with DNA consisting of a nucleotide sequence complementary to the nucleotide sequence of DNA encoding a polypeptide having the amino acid sequence shown in SEQ ID NO: 1 under stringent conditions, which is selected from the group consisting of the following (i) to (ix):

(i) DNA encoding a polypeptide wherein the amino acid residue corresponding to the residue at position 26 from the N terminus of the amino acid sequence shown in SEQ ID NO: 1 is an amino acid residue other than L-alanine;

(ii) DNA encoding a polypeptide wherein the amino acid residue corresponding to the residue at position 31 from the N terminus of the amino acid sequence shown in SEQ ID NO: 1 is an amino acid residue other than L-methionine;

(iii) DNA encoding a polypeptide wherein the amino acid residue corresponding to the residue at position 26 from the N terminus of the amino acid sequence shown in SEQ ID NO: 1 is an amino acid residue other than L-alanine and the amino acid residue corresponding to the residue at position 31 is an amino acid residue other than L-methionine;

(iv) DNA encoding a polypeptide wherein the amino acid residue corresponding to the residue at position 26 from the N terminus of the amino acid sequence shown in SEQ ID NO: 1 is L-valine, L-leucine or L-isoleucine;

(v) DNA encoding a polypeptide wherein the amino acid residue corresponding to the residue at position 31 from the N terminus of the amino acid sequence shown in SEQ ID NO: 1 is L-valine;

(vi) DNA encoding a polypeptide wherein the amino acid residue corresponding to the residue at position 26 from the N terminus of the amino acid sequence shown in SEQ ID NO: 1 is L-valine, L-leucine or L-isoleucine, and the amino acid residue corresponding to the residue at position 31 is L-valine;

(vii) DNA having a nucleotide sequence wherein the region corresponding to the region at positions 76 to 78 from the 5' end of the nucleotide sequence shown in SEQ ID NO: 2 is guanine-thymidine-thymidine, cytosine-thymidine-guanine or adenine-thymidine-cytosine;

(viii) DNA having a nucleotide sequence wherein the region corresponding to the region at positions 91 to 93 from the 5' end of the nucleotide sequence shown in SEQ ID NO: 2 is guanine-thymidine-guanine; and (ix) DNA having a nucleotide sequence wherein the region corresponding to the region at positions 76 to 78 from the 5' end of the nucleotide sequence shown in SEQ ID NO: 2 is guanine-thymidine-thymidine, cytosine-thymidine-guanine or adenine-thymidine-cytosine, and the region corresponding to the region at positions 91 to 93 is guanine-thymidine-guanine, and which encodes a polypeptide having N-acetylglutamate kinase activity.

The DNA capable of hybridization under stringent conditions refers to DNA which is obtained by colony hybridization, plaque hybridization, Southern blot hybridization, or the like using a part or the whole of the DNA consisting of a nucleotide sequence complementary to the nucleotide sequence of DNA encoding a polypeptide having the amino acid sequence shown in SEQ ID NO: 1, 3, 5, 7, 9 or 11, preferably the nucleotide sequence shown in SEQ ID NO: 2, 4, 6, 8, 10 or 12, as a probe. A specific example of such DNA is DNA which can be identified by performing hybridization at 65° C. in the presence of 0.7 to 1.0 mol/l sodium chloride using a filter with colony- or plaque-derived DNA immobilized thereon, and then washing the filter at 65° C. with a 0.1 to 2-fold conc. SSC solution (1-fold conc. SSC solution: 150 mmol/l sodium chloride and 15 mmol/l sodium citrate).

Hybridization can be carried out according to the methods described in Molecular Cloning, A Laboratory Manual, Third Edition, Cold Spring Harbor Laboratory Press (2001) (hereinafter abbreviated as Molecular Cloning, 3rd ed.); Current Protocols in Molecular Biology, John Wiley & Sons (1987-1997) (hereinafter abbreviated as Current Protocols in Molecular Biology); DNA Cloning 1: Core Techniques, A Practical Approach, Second Edition, Oxford University (1995) (hereinafter abbreviated as DNA Cloning), etc. The hybridizable DNA includes DNA having at least 75% homology, preferably 80% or more homology, further preferably 95% or more homology to the nucleotide sequence shown in SEQ ID NO: 2, 4, 6, 8, 10 or 12 as calculated by use of BLAST or FASTA described above.

The microorganisms of the present invention include any microorganisms having the DNA of the present invention. Preferred are microorganisms wherein the transcriptional repression activity of the arginine repressor (ArgR) on the arginine operon is reduced or lost.

The kind of the microorganisms of the present invention is not specifically limited, and examples of the microorganisms include coryneform bacteria.

The coryneform bacteria include microorganisms belonging to the genera *Corynebacterium, Brevibacterium* and *Microbacterium*.

Examples of the microorganisms belonging to the genus *Corynebacterium* are *Corynebacterium glutamicum, Corynebacterium acetoacidophilum, Corynebacterium acetoglutamicum, Corynebacterium callunae, Corynebacterium herculis, Corynebacterium lilium, Corynebacterium melassecola* and *Corynebacterium thermoaminogenes*, specifically, *Corynebacterium glutamicum* ATCC 13032, *Corynebacterium glutamicum* ATCC 13060, *Corynebacterium glutamicum* ATCC 13826 (formerly *Brevibacterium flavum*), *Corynebacterium glutamicum* ATCC 14020 (formerly *Brevibacterium divaricatum*), *Corynebacterium glutamicum* ATCC 13869 (formerly *Brevibacterium lactofermentum*), *Corynebacterium acetoacidophilum* ATCC 13870, *Corynebacterium acetoglutamicum* ATCC 15806, *Corynebacterium callunae* ATCC 15991, *Corynebacterium herculis* ATCC 13868, *Corynebacterium lilium* ATCC 15990, *Corynebacterium melassecola* ATCC 17965 and *Corynebacterium thermoaminogenes* ATCC 9244.

Examples of the microorganisms belonging to the genus *Brevibacterium* are *Brevibacterium saccharolyticum, Brevibacterium immariophilum, Brevibacterium roseum* and *Brevibacterium thiogenitalis*, specifically, *Brevibacterium saccharolyticum* ATCC 14066, *Brevibacterium immariophlum* ATCC 14068, *Brevibacterium roseum* ATCC 13825 and *Brevibacterium thiogenitalis* ATCC 19240.

An example of the microorganisms belonging to the genus *Microbacterium* is *Microbacterium ammoniaphilum*, specifically, *Microbacterium ammoniaphilum* ATCC 15354.

The transcriptional repression activity of ArgR on the arginine operon in the microorganism of the present invention should be reduced compared with its parent strain, preferably to 50% or lower, more preferably 10% or lower, further preferably 5% or lower, most preferably 0%, or lost.

The parent strain may be any microorganism having the ability to form L-arginine, L-ornithine or L-citrulline in which ArgB is subject to feedback inhibition by L-arginine and arginine operon transcription is repressed by ArgR, which may be either a wild-type strain or a strain artificially bred from the wild-type strain. The host microorganism for introducing the DNA of the present invention described below can also be used as the parent strain, so far as it has the above properties.

In the present invention, the term wild-type strain refers to a microorganism which taxonomically belongs to the same species as the microorganism of the present invention and which has the phenotype appearing in nature most frequently.

When the microorganism of the present invention is a microorganism belonging to *Corynebacterium glutamicum*, an example of the wild-type strain is *Corynebacterium glutamicum* ATCC 13032.

The microorganism of the present invention can be obtained by treating a parent strain with a mutagen such as N-methyl-N'-nitro-N-nitrosoguanidine, culturing the obtained strain using a medium comprising arginine hydroxamate (arginine analogue), selecting strains which grow faster than the parent strain, and further selecting strains from microorganisms having enhanced L-arginine productivity compared with that of the parent strain when cultured using an ordinary medium. The microorganism of the present invention can be more conveniently obtained by introducing the DNA of the present invention.

The method for obtaining the microorganism of the present invention by introducing the DNA of the present invention is described below.

The DNA of the present invention can be prepared from DNA having the nucleotide sequence shown in SEQ ID NO: 2 or DNA which has a nucleotide sequence having a high homology to the nucleotide sequence shown in SEQ ID NO: 2 and which encodes a polypeptide having ArgB activity.

"A high homology to the nucleotide sequence shown in SEQ ID NO: 2" refers to at least 75% homology, preferably 80% or more homology, further preferably 95% or more homology.

The DNA having the nucleotide sequence shown in SEQ ID NO: 2 or DNA which has a nucleotide sequence having a high homology to the nucleotide sequence shown in SEQ ID NO: 2 and which encodes a polypeptide having ArgB activity can be prepared from microorganisms having these DNAs, and also can be obtained by chemical synthesis using a DNA synthesizer (Model 8905, PerSeptive Biosystems, Inc.).

Examples of the microorganisms having these DNAs include those belonging to the genus *Corynebacterium*.

Examples of the microorganisms belonging to the genus *Corynebacterium* are *Corynebacterium glutamicum*, *Corynebacterium acetoacidophilum*, *Corynebacterium efficiens* and *Corynebacterium crenatum*, specifically, *Corynebacterium glutamicum* ATCC 13032, *Corynebacterium glutamicum* K65 (FERM BP-1115), *Corynebacterium acetoacidophilum* ATCC 13870 and *Corynebacterium efficiens* JCM 44549. Preferred is *Corynebacterium glutamicum* ATCC 13032 having DNA having the nucleotide sequence shown in SEQ ID NO: 2.

A microorganism having DNA having the nucleotide sequence shown in SEQ ID NO: 2 or DNA which has a nucleotide sequence having a high homology to the nucleotide sequence shown in SEQ ID NO: 2 and which encodes a polypeptide having ArgB activity is cultured by a known method [for example, Mol. Microbiol., 20, 833 (1996)].

After the culturing, the chromosomal DNA of the microorganism is isolated and purified, for example, according to the method of Saito, et al. [Biochim. Biophys. Acta, 72, 619 (1963)].

PCR [PCR Protocols, Academic Press (1990)] is carried out using primers prepared based on the nucleotide sequence of DNA encoding ArgB of *Corynebacterium glutamicum*, which is registered as NCgl1342 in DDBJ/GenBank/EMBL (the nucleotide sequence shown in SEQ ID NO: 2), or the nucleotide sequence of a region containing the said nucleotide sequence (for example, the nucleotide sequence shown in SEQ ID NO: 30), and as a template, the chromosomal DNA isolated and purified to prepare a DNA fragment containing DNA encoding ArgB.

Examples of the primers include DNAs consisting of the nucleotide sequences shown in SEQ ID NOS: 13 to 18 designed based on the nucleotide sequence shown in SEQ ID NO: 30.

Further, a cloned DNA containing DNA encoding ArgB can be obtained from the DNA library which is prepared using the isolated and purified chromosomal DNA according to the methods described in Molecular Cloning, 3rd ed., Current Protocols in Molecular Biology, etc. and then obtaining the desired clone from the DNA library by methods such as colony hybridization, plaque hybridization and Southern hybridization described in laboratory manuals such as Molecular Cloning, 3rd ed., Current Protocols in Molecular Biology and DNA Cloning.

Probes used for hybridization include a known DNA encoding the ArgB of *Corynebacterium glutamicum* or a part of the DNA, DNA which was synthesized based on the nucleotide sequence of the said known DNA, and a DNA fragment obtained by PCR using DNA primers synthesized based on the nucleotide sequence of a known DNA encoding ArgB.

Examples of the probes are DNA having the nucleotide sequence shown in SEQ ID NO: 2 and a DNA fragment amplified by PCR using DNAs consisting of the nucleotide sequences shown in SEQ ID NOS: 13 to 18 as primers and the chromosomal DNA of a microorganism belonging to *Corynebacterium glutamicum* as a template.

The DNA fragment comprising DNA encoding ArgB obtained by colony hybridization, plaque hybridization, Southern hybridization or the like, as such or after cleavage with appropriate restriction enzymes, is inserted into a vector by a conventional method. Then, the nucleotide sequence of the DNA fragment is determined by a conventional sequencing method such as the dideoxy method [Proc. Natl. Acad. Sci. USA, 74, 5463 (1977)] using ABI377 DNA Sequencer (Perkin-Elmer Corp.) or the like.

Further, a DNA fragment having DNA encoding ArgB can be obtained by carrying out PCR [PCR Protocols, Academic Press (1990)] using primers prepared based on the determined nucleotide sequence and the chromosomal DNA as a template.

It is also possible to prepare the desired DNA fragment by chemical synthesis using a DNA synthesizer (e.g., Model 8905, PerSeptive Biosystems) based on the determined nucleotide sequence of the DNA fragment.

An example of the DNA encoding ArgB that can be obtained by the above-described method is DNA having the nucleotide sequence shown in SEQ ID NO: 2.

The DNA of the present invention can be obtained by introducing a site-directed mutation into DNA having the nucleotide sequence shown in SEQ ID NO: 2 or DNA which has a nucleotide sequence having a high homology to the nucleotide sequence shown in SEQ ID NO: 2 and which encodes a polypeptide having ArgB activity by the site-directed mutagenesis method described in Molecular Cloning, 3rd ed.; Current Protocols in Molecular Biology; Nucleic Acids Research, 10, 6487 (1982); Proc. Natl. Acad. Sci. USA, 79, 6409 (1982); Gene, 34, 315 (1985); Nucleic Acids Research, 13, 4431 (1985); Proc. Natl. Acad. Sci. USA, 82, 488 (1985), etc., for example, the method using PCR, according to need.

The thus obtained DNA of the present invention is incorporated into a vector such as a plasmid vector by an ordinary method to prepare the recombinant DNA of the present invention.

As to the vector, there is no specific limitation insofar as it is a vector capable of being introduced into a microorganism into which the DNA of the present invention is introduced (hereinafter referred to as a host microorganism). Examples of suitable vectors are pHSG299 [Gene, 61, 63-74 (1987)], pBTrp2, pBTac1 and pBTac2 (products of Boehringer Mannheim GmbH), pHelixl (Roche Diagnostics Corp.), pKK233-2 (Amersham Pharmacia Biotech), pSE280 (Invitrogen Corp.), pGEMEX-1 (Promega Corp.), pQE-8 (Qiagen, Inc.), pET-3 (Novagen, Inc.), pKYP10 (Japanese Published Unexamined Patent Application No. 110600/83), pKYP200 [Agric. Biol. Chem., 48, 669 (1984)], pLSA1 [Agric. Biol. Chem., 53, 277 (1989)], pGEL1 [Proc. Natl. Acad. Sci. USA, 82, 4306 (1985)], pBluescript II SK(+), pBluescript II KS(−) (Stratagene), pTrS30 [prepared from *Escherichia coli* JM109/pTrS30 (FERM BP-5407)], pTrS32 [prepared from *Escherichia coli* JM109/pTrS32 (FERM BP-5408)], pPAC31 (WO98/12343 pamphlet), pUC19 [Gene, 33, 103 (1985)], pSTV28 (Takara Shuzo Co., Ltd.), pUC118 (Takara Shuzo Co., Ltd.), pPA1 (Japanese Published Unexamined Patent Application No. 233798/88), pCG116, pCG1 (Japanese Published Unexamined Patent Application No. 277082/94) and pCS299P (WO00/63388 pamphlet). It is preferable to use vectors incapable of autonomous replication in a host microorganism because the recombinant DNA of the present invention can be integrated into the chromosome of the host microorganism by using such vectors.

As the host microorganisms, the above microorganisms can be used.

There is no specific limitation as to the vectors incapable of autonomous replication in a host microorganism. Preferred is a vector having a gene involved in antibiotic resistance, which facilitates selection of a microorganism in which the recombinant DNA of the present invention has been integrated on the chromosome by homologous recombination. More preferred is a vector having DNA encoding levansucrase (EC: 2.4.1.10) derived from *Bacillus subtilis* (sacB), which facilitates selection of a microorganism wherein the DNA encoding ArgB originally existing on the chromosome of the host microorganism has been replaced by the DNA of the present invention. An example of such vector is plasmid pESB30 described in Example 1.

The recombinant DNA of the present invention is introduced into a host microorganism.

Introduction of a mutation which reduces or obliterates ArgR activity of the microorganism of the present invention may be carried out either before or after the introduction of the DNA of the present invention into the host microorganism.

The reduction or loss of ArgR activity can be achieved by treating a microorganism whose ArgR activity is to be reduced or lost with a mutagen (e.g. N-methyl-N'-nitro-N-nitrosoguanidine) and selecting strains whose L-arginine productivity is enhanced compared with that before the mutagenesis, or alternatively, by introducing a nucleotide substitution, deletion or addition into DNA encoding ArgR by the method similar to that for introducing a site-directed mutation into DNA encoding ArgB.

The nucleotide substitution, deletion or addition may be introduced at any site so far as ArgR activity can be reduced or lost, but is preferably introduced at a site in the L-arginine-binding region of the DNA encoding ArgR or a region containing the binding region so that the activity can be efficiently reduced or lost.

An example of the L-arginine-binding region is the region at positions 45 to 240 of the nucleotide sequence shown in SEQ ID NO: 19, which is the nucleotide sequence of DNA encoding ArgR of *Corynebacterium glutamicum* ATCC 13032. In the DNAs encoding ArgR of other microorganisms, the L-arginine-binding region is in the region corresponding to the above region or in its vicinity.

The number of nucleotides which are substituted, deleted or added is not specifically limited insofar as it is a number adequate for reduction or loss of ArgR activity.

Introduction of the DNA of the present invention into a host microorganism can be carried out by any of the methods capable of introducing the recombinant DNA of the present invention into a host microorganism.

For example, methods such as electroporation [Appl. Microbiol. Biotech., 52, 541 (1999)] and the protoplast method [J. Bacteriol., 159, 306 (1984)] can be used.

As wild-type ArgB is subject to feedback inhibition by L-arginine, microorganisms in which the feedback inhibition is not reduced or canceled show a slower growth rate than microorganisms in which the feedback inhibition is reduced or canceled in a medium comprising arginine hydroxamate (arginine analogue). Microorganisms in which ArgR activity is not reduced or lost have a lower ArgB expression level due to the transcription repression of arginine operon by accumulation of L-arginine and show a further slower growth rate in a medium comprising arginine hydroxamate.

Therefore, it is possible to confirm that the DNA of the present invention was introduced into a microorganism obtained by introducing the DNA of the present invention into a host microorganism by the above method by checking that the growth rate of the microorganism is enhanced compared with that of the host microorganism when the growth rate of the microorganism and that of the host microorganism are compared in a medium comprising arginine hydroxamate. The confirmation can also be made by preparing a plasmid or a chromosome from the microorganism by a conventional method and then examining the nucleotide sequence.

Reduction or loss of ArgR activity of the microorganism can be confirmed by comparing the expression of arginine operon in the microorganism and the host microorganism by Northern hybridization (Molecular Cloning, 3rd ed.) or the like. The probes used for Northern hybridization include DNA having a part or the whole of the nucleotide sequence of genes constituting the arginine operon, for example, the above-described DNA used to select the DNA encoding ArgB from a DNA library.

The confirmation can also be made by using a microorganism carrying a reporter gene incorporated into the arginine operon as a host microorganism, and comparing the expression amount of the reporter gene with that of the host microorganism.

The microorganism of the present invention may be any microorganism having the DNA of the present invention in which ArgR activity is reduced or lost. When the microorganism of the present invention is used for production of L-ornithine, it is desirable that the activity of ornithine carbamoyltransferase, which is an enzyme on the biosynthetic pathway of L-arginine (EC: 2.1.3.3, hereinafter referred to as ArgF), in the microorganism is lost or reduced compared with that of the parent strain. A strain in which ArgF activity is lost or reduced compared with that of the parent strain may be obtained by mutagenesis in the same way as the method for introducing a mutation into ArgB and ArgR, or by introducing a nucleotide substitution, deletion or addition into DNA encoding ArgF using the same method as the method for introducing a site-directed mutation into ArgB and ArgR. The DNA encoding ArgF is known and the nucleotide sequence information described, for example, in DDBJ/GenBank/EMBL can be used. An example of the DNA encoding ArgF is DNA having the nucleotide sequence shown in SEQ ID NO: 31.

When the microorganism of the present invention is used for production of L-citrulline, it is desirable that the activity of argininosuccinate synthase, which is an enzyme on the biosynthetic pathway of L-arginine (EC: 6.3.4.5, hereinafter referred to as ArgG), in the microorganism is lost or reduced compared with that of the parent strain. A strain in which ArgG activity is lost or reduced compared with that of the parent strain may be obtained by mutagenesis in the same way as the method for introducing a mutation into ArgB and ArgR, or by introducing a nucleotide substitution, deletion or addition into DNA encoding ArgG using the same method as the method for introducing a site-directed mutation into ArgB and ArgR. The DNA encoding ArgG is known and the nucleotide sequence information described, for example, in DDBJ/GenBank/EMBL can be used. An example of the DNA encoding ArgG is DNA having the nucleotide sequence shown in SEQ ID NO: 32.

L-Arginine, L-ornithine or L-citrulline can be produced by culturing the microorganism of the present invention in a medium, allowing L-arginine, L-ornithine or L-citrulline to form and accumulate in the culture, and recovering L-arginine, L-ornithine or L-citrulline.

As the method for culturing the microorganism of the present invention in a medium, any ordinary methods used for culturing a microorganism may be used.

As the medium, any of natural media and synthetic media can be used insofar as it is a medium suitable for efficient culturing of the microorganism of the present invention which contains carbon sources, nitrogen sources, inorganic salts, etc. which can be assimilated by the microorganism.

As the carbon sources, any carbon sources that can be assimilated by the microorganism of the present invention can be used. Examples of suitable carbon sources include carbohydrates such as glucose, fructose, sucrose, maltose, molasses containing them, starch and starch hydrolyzate; organic acids such as acetic acid, lactic acid and succinic acid; and alcohols such as ethanol and propanol.

Examples of the nitrogen sources include ammonia, ammonium salts of organic or inorganic acids such as ammonium chloride, ammonium sulfate, ammonium acetate and ammonium carbonate, other nitrogen-containing compounds, peptone, meat extract, yeast extract, corn steep liquor, casein hydrolyzate, soybean cake, soybean cake hydrolyzate, and various fermented microbial cells and digested products thereof.

Examples of the inorganic salts include potassium dihydrogenphosphate, dipotassium hydrogenphosphate, magnesium phosphate, magnesium sulfate, sodium chloride, iron sulfate, manganese sulfate, copper sulfate and calcium carbonate.

Further, micronutrients such as biotin, thiamine, nicotinamide and nicotinic acid can be added according to need. These micronutrients may be supplied by meat extract, yeast extract, corn steep liquor, Casamino acid, etc.

Culturing is carried out under aerobic conditions, for example, by shaking culture or submerged spinner culture under aeration. The culturing temperature is preferably 20 to 42° C., more preferably 30 to 40° C. The pH of the medium is in the range of 5 to 9, and is preferably maintained around neutral. The pH adjustment is carried out by using an inorganic or organic acid, an alkali solution, urea, calcium carbonate, ammonia, pH buffer, etc.

When the recombinant DNA of the present invention used for preparation of the microorganism of the present invention has an inducible promoter, an inducer suited for the promoter may be added to the medium, if necessary. For example, when a recombinant DNA having lac promoter is used, isopropyl-β-D-thiogalactopyranoside or the like may be added to the medium; and when a recombinant DNA having trp promoter is used, indoleacrylic acid or the like may be added.

Culturing is usually carried out for 1 to 6 days and L-arginine, L-ornithine or L-citrulline is formed and accumulated in the culture.

After the completion of culturing, precipitates such as cells are removed from the culture, and L-arginine, L-ornithine or L-citrulline accumulated in the culture can be recovered by combining known methods such as active carbon treatment and ion-exchange resin treatment.

Certain embodiments of the present invention are illustrated in the following examples. These examples are not to be construed as limiting the scope of the present invention.

EXAMPLE 1

Construction of a Plasmid for Substitution of Amino Acids in ArgB (1) Preparation of a Vector for Homologous Recombination Plasmid pHSG299 carrying a gene conferring resistance to kanamycin [Gene, 61, 63 (1987)] was treated with PstI, and a DNA fragment of 2.6 kilobase pair (hereinafter abbreviated as kb) containing levansucrase gene sacB derived from *Bacillus subtilis* [Mol. Microbiol., 6, 1195 (1992)] was ligated to the cleavage site of the plasmid pHSG299 to obtain plasmid pESB30.

pESB30 was treated with BamHI (Takara Shuzo Co., Ltd.) and subjected to agarose gel electrophoresis, followed by extraction and purification using GENECLEAN Kit (BIO 101). Both ends of the obtained DNA fragment were blunted using a DNA blunting kit (DNA Blunting Kit, Takara Shuzo Co., Ltd.) according to the attached protocol. The blunted DNA fragment was treated with phenol/chloroform, concentrated by ethanol precipitation, and then subjected to reaction in the presence of Taq polymerase (Roche Diagnosis) and dTTP at 70° C. for 2 hours for addition of one thymine base to the 3' end to prepare plasmid pESB30-T.

(2) Preparation of DNA Encoding ArgB in Which Alanine at Position 26 is Substituted by Valine DNA having the nucleotide sequence at positions 19 to 38 of the nucleotide sequence shown in SEQ ID NO: 30 (DNA consisting of the nucleotide sequence shown in SEQ ID NO: 13) and DNA having a sequence complementary to the nucleotide sequence at positions 1027 to 1047 of the nucleotide sequence shown in SEQ ID NO: 30 (DNA consisting of the nucleotide sequence shown in SEQ ID NO: 14) were synthesized using a DNA synthesizer.

The nucleotide sequence at positions 451 to 1332 of the nucleotide sequence shown in SEQ ID NO: 30 is a region encoding a polypeptide having the amino acid sequence shown in SEQ ID NO: 1, which is ArgB of *Corynebacterium glutamicum*. The nucleotide sequence of the region is shown in SEQ ID NO: 2.

DNA consisting of a nucleotide sequence complementary to the nucleotide sequence at positions 68 to 89 of the nucleotide sequence shown in SEQ ID NO: 4 (the sequence of SEQ ID NO: 4 is a sequence wherein cytosine at position 77 of the nucleotide sequence shown in SEQ ID NO: 2 was substituted by thymidine and encodes the amino acid sequence shown in SEQ ID NO: 3, wherein alanine at position 26 of the amino acid sequence shown in SEQ ID NO: 1 was substituted by valine) (DNA consisting of the nucleotide sequence shown in SEQ ID NO: 15) and DNA consisting of the nucleotide sequence at positions 65 to 87 of the nucleotide sequence shown in SEQ ID NO: 4 (DNA consisting of the nucleotide sequence shown in SEQ ID NO: 16) were synthesized using a DNA synthesizer.

The chromosomal DNA of *Corynebacterium glutamicum* ATCC 13032 was prepared according to the method of Saito, et al. [Biochim. Biophys. Acta, 72, 619 (1963)], and two kinds of PCR were carried out using the chromosomal DNA as a template, a combination of the DNA consisting of the nucleotide sequence shown in SEQ ID NO: 13 and the DNA consisting of the nucleotide sequence shown in SEQ ID NO: 15 and a combination of the DNA consisting of the nucleotide sequence shown in SEQ ID NO: 14 and the DNA consisting of the nucleotide sequence shown in SEQ ID NO: 16, respectively, as a set of primers, Pfu turbo DNA polymerase (Stratagene) and the attached buffer. Two ca. 0.5 kb PCR products obtained by the PCR were respectively subjected to agarose gel electrophoresis, and extracted and purified using GENECLEAN Kit (BIO 101).

PCR was further carried out using both the purified products as templates, and the DNA consisting of the nucleotide sequence shown in SEQ ID NO: 13 and the DNA consisting of the nucleotide sequence shown in SEQ ID NO: 14 as a set of primers. The obtained PCR product was subjected to agarose gel electrophoresis, and extracted and purified using GENECLEAN Kit to obtain a ca. 1.0 kb DNA fragment. The nucleotide sequence of the DNA fragment was determined using a sequencer and it was confirmed that the DNA fragment had the nucleotide sequence shown in SEQ ID NO: 4.

(3) Preparation of DNA Encoding ArgB in Which Methionine at Position 31 is Substituted by Valine DNA consisting of a nucleotide sequence complementary to the nucleotide sequence at positions 83 to 102 of the nucleotide sequence shown in SEQ ID NO: 10 (the sequence of SEQ ID NO: 10 is a sequence wherein adenine at position 91 of the nucleotide sequence shown in SEQ ID NO: 2 was substituted by guanine and encodes a sequence wherein methionine at position 31 of the amino acid sequence shown in SEQ ID NO: 1 was substituted by valine) (DNA consisting of the nucleotide sequence shown in SEQ ID NO: 17) and DNA consisting of the nucleotide sequence at positions 79 to 99 of the nucleotide sequence shown in SEQ ID NO: 10 (DNA consisting of the nucleotide sequence shown in SEQ ID NO: 18) were synthesized using a DNA synthesizer.

The same procedure as in (2) was carried out except that a combination of the DNA consisting of the nucleotide sequence shown in SEQ ID NO: 13 and the DNA having the nucleotide sequence shown in SEQ ID NO: 17 and a combination of the DNA having the nucleotide sequence shown in SEQ ID NO: 14 and the DNA consisting of the nucleotide sequence shown in SEQ ID NO: 18 were respectively used as a set of primers to obtain a ca. 1.0 kb DNA fragment.

The nucleotide sequence of the obtained DNA fragment was determined using a sequencer and it was confirmed that the DNA fragment had the nucleotide sequence shown in SEQ ID NO: 10.

(4) Construction of a Plasmid for Substitution of One Amino Acid in ArgB

Each of the DNA fragments respectively having the nucleotide sequences shown in SEQ ID NOS: 4 and 10 obtained in the above (2) and (3) was treated in the presence of Taq polymerase (Boehringer Mannheim GmbH) and DATP at 72° C. for 10 minutes for addition of one adenine base to the 3' end of the DNA fragment.

Plasmid pESB30-T was mixed with each of the DNA fragments prepared by adding an adenine residue to the DNA fragments having DNAs having the nucleotide sequences shown in SEQ ID NOS: 4 and 10, respectively, and ligase reaction was carried out using Ligation Kit Ver. 1 (Takara Shuzo Co., Ltd.). By using each of the obtained reaction products, *Escherichia coli* DH5α (Toyobo Co., Ltd.) was transformed according to a conventional method. The strain was cultured on LB agar medium [containing 10 g of Bacto-tryptone (Difco), 5 g of yeast extract (Difco), 10 g of sodium chloride and 16 g of Bacto-agar (Difco) in 1 liter of water, pH 7.0] containing 20 µg/ml kanamycin to select a transformant. The transformant was cultured overnight using LB medium containing 20 µg/ml kanamycin, and a plasmid was prepared from the obtained culture by the alkali SDS method (Molecular Cloning, 3rd ed.). The nucleotide sequences of the obtained plasmids were determined using a sequencer and it was confirmed that the DNAs having the nucleotide sequences shown in SEQ ID NOS: 4 and 10, respectively, were inserted into pESB30-T in the respective plasmids.

The plasmid having the DNA having the nucleotide sequence shown in SEQ ID NO: 4 was designated as pEargB26 and the plasmid having the DNA having the nucleotide sequence shown in SEQ ID NO: 10 was designated as pEargB31.

(5) Construction of a Plasmid for Substitution of Two Amino Acids in ArgB

The same procedure as in the above (2) was carried out except that a combination of the DNA consisting of the nucleotide sequence shown in SEQ ID NO: 13 and the DNA consisting of the nucleotide sequence shown in SEQ ID NO: 15 and a combination of the DNA consisting of the nucleotide sequence shown in SEQ ID NO: 14 and the DNA consisting of the nucleotide sequence shown in SEQ ID NO: 16 were respectively used as a set of primers and pEargB31 was used as a template to obtain a ca. 1.0 kb DNA fragment. The nucleotide sequence of the DNA fragment was determined using a sequencer and it was confirmed that the DNA fragment had the nucleotide sequence shown in SEQ ID NO: 12.

The same procedure as in the above (4) was carried out except that the DNA having the nucleotide sequence shown in SEQ ID NO: 12 was used to obtain plasmid pEargB2631 wherein the DNA having the nucleotide sequence shown in SEQ ID NO: 12 was incorporated into pESB30-T.

The DNA shown in SEQ ID NO: 12 is DNA encoding the amino acid sequence shown in SEQ ID NO: 11, which is DNA encoding the amino acid sequence wherein alanine at position 26 and methionine at position 31 of the amino acid sequence shown in SEQ ID NO: 1 are respectively substituted by valine.

Example 2

Introduction of Amino Acid Substitutions into ArgB on the Chromosome (1) Introduction of Amino Acid Substitutions into ArgB on the Chromosome of a Wild-Type Strain

*Corynebacterium glutamicum* ATCC 13032 was transformed by electroporation according to the method of Rest et al. [Appl. Microbiol. Biotech., 52, 541 (1999)] using plasmids pEargB26, pEargB31 and pEargB2631 prepared in Example 1, respectively, to select kanamycin-resistant strains. A chromosome was prepared from one of the kanamycin-resistant strains and examined by Southern hybridization (Molecular Cloning, 3rd ed.), whereby it was confirmed that pEargB26, pEargB31 and pEargB2631 were respectively integrated into the chromosome of the strains by Campbell-type homologous recombination. In such strains, the DNA encoding ArgB which is originally present on the chromosome and the DNA of the present invention exist close to each other on the chromosome and the second homologous recombination is apt to take place between them.

As levansucrase encoded by sacB converts sucrose into a suicide substrate, a microorganism having sacB cannot grow on a medium containing sucrose. However, when the second homologous recombination took place between the DNA encoding ArgB which is originally present on the chromosome and the DNA of the present invention, one of these DNAs is deleted together with sacB and so the resulting strain can grow on the medium containing sucrose. When the DNA encoding ArgB which is originally present on the chromosome is deleted, a microorganism wherein the DNA encoding ArgB which is originally present on the chromosome of the host microorganism is substituted by the DNA of the present invention can be obtained.

By utilizing this, the above transformant was spread on Suc agar medium [comprising 100 g of sucrose, 7 g of meat extract, 10 g of peptone, 3 g of sodium chloride, 5 g of yeast extract (Difco) and 15 g of Bacto-agar (Difco) in 1 liter of water, pH 7.2] and cultured at 30° C. for one day to select a colony growing thereon.

The chromosomal DNA was prepared from the thus obtained colony, and PCR was carried out using the chromosomal DNA as a template, the DNA consisting of the nucleotide sequence shown in SEQ ID NO: 13 and the DNA consisting of the nucleotide sequence shown in SEQ ID NO: 14 as a set of primers, Pfu turbo DNA polymerase (Stratagene) and the attached buffer. The nucleotide sequence of the PCR product was determined using a sequencer.

Thus, a strain wherein the DNA encoding ArgB on the chromosome is substituted by the DNA having the nucleotide sequence shown in SEQ ID NO: 4 was obtained from the strains into which pEargB26 was introduced, and the strain was designated as strain B26.

In the same manner, a strain wherein the DNA encoding ArgB on the chromosome is substituted by the DNA having the nucleotide sequence shown in SEQ ID NO: 10 was obtained from the strains into which pEargB31 was introduced, and the strain was designated as strain B31.

Further, a strain wherein the DNA encoding ArgB on the chromosome is substituted by the DNA having the nucleotide sequence shown in SEQ ID NO: 12 was obtained from the strains into which pEargB2631 was introduced, and the strain was designated as strain B2631.

(2) Construction of a Plasmid for Deletion of an Internal Sequence of ArgR

The chromosomal DNA of *Corynebacterium glutamicum* ATCC 13032 was prepared according to the method of Saito, et al. [Biochim. Biophys. Acta, 72, 619 (1963)].

The following DNAs were synthesized using a DNA synthesizer: DNA consisting of the nucleotide sequence at positions 43 to 62 of the nucleotide sequence of DNA encoding ArgR of *Corynebacterium glutamicum* shown in SEQ ID NO: 19 (DNA consisting of the nucleotide sequence shown in SEQ ID NO: 20), DNA consisting of a sequence complementary to the nucleotide sequence at positions 1421 to 1440 of the nucleotide sequence shown in SEQ ID NO: 19 (DNA consisting of the nucleotide sequence shown in SEQ ID NO: 21), DNA consisting of a sequence complementary to the nucleotide sequence prepared by adding a tag sequence to the nucleotide sequence at positions 539 to 559 of the nucleotide sequence shown in SEQ ID NO: 19 (DNA consisting of the nucleotide sequence shown in SEQ ID NO: 22) and DNA consisting of the nucleotide sequence prepared by adding a tag sequence to the nucleotide sequence at positions 941 to 961 of the nucleotide sequence shown in SEQ ID NO: 19 (DNA consisting of the nucleotide sequence shown in SEQ ID NO: 23).

The nucleotide sequence shown in SEQ ID NO: 19 is a nucleotide sequence containing the nucleotide sequence of DNA encoding ArgR of *Corynebacterium glutamicum*. Two kinds of PCR were carried out using the prepared chromosomal DNA as a template, a combination of the DNA consisting of the nucleotide sequence shown in SEQ ID NO: 20 and the DNA consisting of the nucleotide sequence shown in SEQ ID NO: 22 and a combination of the DNA consisting of the nucleotide sequence shown in SEQ ID NO: 21 and the DNA consisting of the nucleotide sequence shown in SEQ ID NO: 23, respectively, as a set of primers, Pfu turbo DNA polymerase (Stratagene) and the attached buffer. Two ca. 0.5 kb PCR products obtained by the PCR were respectively subjected to agarose gel electrophoresis, and extracted and purified using GENECLEAN Kit (BIO 101).

PCR was further carried out using both the purified products as templates, the DNA consisting of the nucleotide sequence shown in SEQ ID NO: 20 and the DNA consisting of the nucleotide sequence shown in SEQ ID NO: 21 as a set of primers, Pfu turbo DNA polymerase (Stratagene) and the attached buffer. The obtained PCR product was subjected to agarose gel electrophoresis, and extracted and purified using GENECLEAN Kit (BIO 101), whereby a ca. 1.0 kb DNA fragment in which the region at positions 560 to 940 of the nucleotide sequence shown in SEQ ID NO: 19 encoding ArgR was deleted was obtained.

This fragment was incorporated into plasmid pESB30-T according to the method described in Example 1 to obtain plasmid pEdel-argR.

(3) Construction of a Strain Having a Deletion of an Internal Sequence of ArgR

The same procedure as in the above (1) was carried out except that plasmid pEdel-argR was used. This procedure yielded a strain in which the DNA encoding ArgR on the chromosome of *Corynebacterium glutamicum* ATCC 13032 was substituted by the DNA wherein the region at positions 560 to 940 of the nucleotide sequence shown in SEQ ID NO: 19 was deleted. The obtained strain was designated as strain R.

(4) Introduction of Amino Acid Substitutions into ArgB on the Chromosome of a Strain Having a Deletion of an Internal Sequence of ArgR The same procedure as in the above (1) was carried out except that strain R was used as a host and pEargB26, pEargB31 and pEargB2631 were used as plasmids. This procedure yielded strains in which the DNA encoding ArgB on the chromosome was substituted by the DNA having the nucleotide sequence shown in SEQ ID NO: 4, 10 or 12 and the DNA encoding ArgR on the chromosome was substituted by the DNA wherein the region at positions 560 to 940 of the nucleotide sequence shown in SEQ ID NO: 19 was deleted. The strains were designated as strain RB26, strain RB31 and strain RB2631, respectively.

Example 3

L-Arginine, L-Ornithine and L-Citrulline Production Test Using Strains Having Amino Acid Substitutions in ArgB The strains B26, B31, B2631, R, RB26, RB31 and RB2631 obtained in Example 2 were separately cultured on BY agar medium (a medium comprising 7 g of meat extract, 10 g of peptone, 3 g of sodium chloride, 5 g of yeast extract and 15 g of Bacto-agar in 1 liter of water, pH 7.2) at 30° C. for 24 hours.

Cells of each of the strains that grew on the BY agar medium were inoculated into a test tube containing 6 ml of a seed medium (a medium which was prepared by adding 10 g of calcium carbonate to a medium containing 25 g of sucrose, 20 g of corn steep liquor, 20 g of peptone, 10 g of yeast extract, 0.5 g of magnesium sulfate heptahydrate, 2 g of potassium dihydrogenphosphate, 3 g of urea, 8 g of ammonium sulfate, 1 g of sodium chloride, 20 mg of nicotinic acid, 10 mg of iron sulfate heptahydrate, 10 mg of calcium pantothenate, 1 mg of zinc sulfate heptahydrate, 1 mg of copper sulfate pentahydrate, 1 mg of thiamine hydrochloride and 100 μg of biotin in 1 liter of water and adjusted to pH 7.2 with an aqueous solution of sodium hydroxide), followed by shaking culture at 32° C. for 24 hours.

Each of the obtained seed cultures (2 ml) was inoculated into a flask with baffles containing 20 ml of a main culture medium (a medium which was prepared by adding 30 g of calcium carbonate to a medium containing 60 g of glucose, 5 g of corn steep liquor, 30 g of ammonium sulfate, 8 g of potassium chloride, 2 g of urea, 0.5 g of potassium dihydrogenphosphate, 0.5 g of dipotassium hydrogenphosphate, 1 g of magnesium sulfate heptahydrate, 1 g of sodium chloride, 20 mg of iron sulfate heptahydrate, 20 mg of nicotinic acid, 20 mg of β-alanine, 10 mg of manganese sulfate pentahydrate, 10 mg of thiamine hydrochloride and 200 μg of biotin in 1 liter of water and adjusted to pH 7.7 with an aqueous solution of sodium hydroxide), followed by shaking culture at 32° C. for 48 hours.

The same procedure was carried out using *Corynebacterium glutamicum* ATCC 13032 and the obtained culture was used as a control.

After the cells were removed from the culture by centrifugation, the amounts of L-arginine, L-ornithine and L-citrulline accumulated in the supernatant were determined by high performance liquid chromatography (HPLC). The results are shown in Table 1.

TABLE 1

| Strain | OD 660 nm | L-Arginine (g/l) | L-Ornithine (g/l) | L-Citrulline (g/l) |
|---|---|---|---|---|
| ATCC 13032 | 48 | 0.0 | 0.0 | 0.0 |
| B26 | 44 | 0.0 | 0.0 | 0.0 |
| B31 | 46 | 0.0 | 0.0 | 0.0 |
| B2631 | 45 | 0.0 | 0.0 | 0.0 |
| R | 45 | 0.0 | 0.0 | 0.0 |
| RB26 | 43 | 3.0 | 0.2 | 1.0 |
| RB31 | 46 | 2.0 | 0.1 | 0.8 |
| RB2631 | 38 | 4.5 | 0.3 | 2.0 |

As shown in Table 1, production of L-arginine, L-ornithine and L-citrulline was not confirmed with the strains ATCC 13032 (control), B26, B31, B2631 and R. On the contrary, production of L-arginine, L-ornithine and L-citrulline was confirmed with the strains RB26, RB31 and RB2631.

Example 4

Construction of L-Ornithine-Producing Strains Having an Amino Acid Substitution in ArgB (1) Construction of DNA for Construction of a Plasmid for Deletion of an Internal Sequence of ArgF DNA consisting of the nucleotide sequence prepared by adding a tag sequence to the nucleotide sequence at positions 21 to 43 of the nucleotide sequence shown in SEQ ID NO: 31 (DNA consisting of the nucleotide sequence shown in SEQ ID NO: 24) and DNA consisting of a sequence complementary to the nucleotide sequence prepared by adding a tag sequence to the nucleotide sequence at positions 1366 to 1385 of the nucleotide sequence shown in SEQ ID NO: 31 (DNA consisting of the nucleotide sequence shown in SEQ ID NO: 25) were synthesized using a DNA synthesizer.

The nucleotide sequence shown in SEQ ID NO: 31 is a nucleotide sequence containing the nucleotide sequence of DNA encoding ArgF of *Corynebacterium glutamicum*.

(2) Construction of a Plasmid for Deletion of an Internal Sequence of ArgF: 1

The chromosomal DNA of *Corynebacterium glutamicum* ATCC 13032 was prepared according to the method of Saito, et al. [Biochim. Biophys. Acta, 72, 619 (1963)].

PCR was carried out using the chromosomal DNA as a template, the DNA consisting of the nucleotide sequence shown in SEQ ID NO: 24 and the DNA consisting of the nucleotide sequence shown in SEQ ID NO: 25 as a set of primers, Pfu turbo DNA polymerase (Stratagene) and the attached buffer. A ca. 1.4 kb DNA fragment obtained by the PCR was treated with BamHI (Takara Shuzo Co., Ltd.), subjected to agarose gel electrophoresis, and extracted and purified using GENECLEAN Kit (BIO 101). The obtained DNA fragment was mixed with pUC119 (Takara Shuzo Co., Ltd.) previously cleaved by BamHI, and ligase reaction was carried out using Ligation Kit Ver. 1 (Takara Shuzo Co., Ltd.).

By using the reaction product, *Escherichia coli* DH5α (Toyobo Co., Ltd.) was transformed according to the method described in Molecular Cloning, 3rd ed. The strain was cultured on LB agar medium containing 50 μg/ml ampicillin to select a transformant. The transformant was cultured overnight using LB medium containing 50 μg/ml ampicillin, and a plasmid was prepared from the obtained culture by the alkali SDS method (Molecular Cloning, 3rd ed.). The plasmid was cleaved by NcoI and subjected to ligase reaction using Ligation Kit Ver. 1 (Takara Shuzo Co., Ltd.) for self-circularization. *Escherichia coli* DH5α was transformed using the reaction product and a plasmid was prepared from the obtained transformant. The structure of the plasmid was examined using restriction enzymes, whereby it was confirmed that the plasmid contained a DNA fragment wherein 369 base pairs were deleted in the DNA encoding ArgF.

(3) Construction of a Plasmid for Deletion of an Internal Sequence of ArgF: 2

PCR was carried out using the obtained plasmid as a template, the DNA consisting of the nucleotide sequence shown in SEQ ID NO: 24 and the DNA consisting of the nucleotide sequence shown in SEQ ID NO: 25 as a set of primers, Pfu turbo DNA polymerase (Stratagene) and the attached buffer to obtain a ca. 1.0 kb DNA fragment. The DNA fragment was subjected to reaction in the presence of Taq DNA polymerase (Boehringer Mannheim GmbH) and DATP at 72° C. for 10 minutes to add one adenine base to the 3' end. Ligase reaction was carried out using pESB30-T prepared in Example 1, the DNA fragment having the added adenine and Ligation Kit Ver. 1 (Takara Shuzo Co., Ltd.). The obtained plasmid was designated as pEargF.

(4) Construction of Strains Having an Amino Acid Substitution in ArgB and a Deletion of an Internal Sequence of ArgF The same procedure as in Example 2 (1) was carried out except that the strains B26, B31, R, RB26, RB31 and ATCC 13032 were used as hosts and pEargF was used as a plasmid. This procedure yielded strains in which the DNA encoding ArgF on the chromosome was substituted by the DNA wherein 369 base pairs in the DNA encoding ArgF were deleted, and the obtained strains were designated as strains FB26, FB31, FR, FRB26, FRB31 and F, respectively.

Example 5

L-Ornithine Production Test Using Strains Having an Amino Acid Substitution in ArgB and a Deletion of an Internal Sequence of ArgF The strains FB26, FB31, FR, FRB26, FRB31 and F prepared in Example 4 and the strain ATCC 13032 were separately cultured on BY agar medium at 30° C. for 24 hours. Each of the strains was inoculated into a test tube containing 6 ml of a seed medium (a medium which was prepared by adding 10 g of calcium carbonate to a medium containing 25 g of glucose, 0.5 g of potassium dihydrogenphosphate, 1.5 g of dipotassium hydrogenphosphate, 0.5 g of magnesium sulfate, 20 g of peptone, 3 g of urea, 50 μg of biotin and 0.3 g of L-arginine in 1 liter of water), followed by shaking culture at 32° C. for 24 hours. Each of the obtained seed cultures (2 ml) was inoculated into a flask with baffles containing 20 ml of a main culture medium (a medium which was prepared by adding 30 g of calcium carbonate to a medium containing 100 g of glucose, 30 g of ammonium sulfate, 0.6 g of magnesium sulfate, 0.5 g of potassium dihydrogenphosphate, 0.25 g of L-arginine, 16 mg of iron sulfate heptahydrate, 16 mg of manganese sulfate pentahydrate, 4.9 mg of zinc sulfate heptahydrate, 4.9 mg of copper sulfate pentahydrate, 16 mg of calcium chloride, 16 mg of β-alanine, 8 mg of thiamine hydrochloride, 180 a g of biotin and 16 g of corn steep liquor in 930 ml of water and adjusted to pH 7.2 with an aqueous solution of sodium hydroxide), followed by shaking culture at 32° C. for 48 hours.

After the cells were removed from the culture by centrifugation, the amount of L-ornithine accumulated in the supernatant was determined by high performance liquid chromatography (HPLC). The results are shown in Table 2.

TABLE 2

| Strain | OD 660 nm | L-Ornithine (g/l) |
|---|---|---|
| ATCC 13032 | 49 | 0.0 |
| F | 22 | 5.0 |
| FB26 | 22 | 5.3 |
| FB31 | 21 | 5.2 |
| FR | 22 | 5.3 |
| FRB26 | 21 | 6.2 |
| FRB31 | 20 | 6.0 |

As is clear from Table 2, the production amount of L-ornithine by using the strain FRB26 having the DNA having the nucleotide sequence shown in SEQ ID NO: 4 and deletions in ArgF and ArgR and the strain FRB31 having the DNA having the nucleotide sequence shown in SEQ ID NO: 10 and deletions in ArgF and ArgR was clearly higher than that of L-ornithine by using the other strains.

Example 6

Construction of Strains Having a Deletion of an Internal Sequence of ArgR Wherein Alanine at position 26 of ArgB is Substituted by Leucine or Isoleucine (1) Construction of a Plasmid for Substitution of One Amino Acid in ArgB DNA consisting of a nucleotide sequence complementary to the nucleotide sequence at positions 68 to 89 of the nucleotide sequence shown in SEQ ID NO: 6 (the sequence of SEQ ID NO: 6 is a sequence wherein the region at positions 76 to 78 of the nucleotide sequence shown in SEQ ID NO: 2 is substituted by ctg and encodes the amino acid sequence shown in SEQ ID NO: 5, wherein alanine at position 26 of the amino acid sequence shown in SEQ ID NO: 1 is substituted by leucine) (DNA consisting of the nucleotide sequence shown in SEQ ID NO: 26) and DNA consisting of the nucleotide sequence at positions 65 to 87 of the nucleotide sequence shown in SEQ ID NO: 6 (DNA consisting of the nucleotide sequence shown in SEQ ID NO: 27) were synthesized using a DNA synthesizer.

In the same manner, DNA consisting of a nucleotide sequence complementary to the nucleotide sequence at positions 68 to 89 of the nucleotide sequence shown in SEQ ID NO: 8 (the sequence of SEQ ID NO: 8 is a sequence wherein the region at positions 76 to 78 of the nucleotide sequence shown in SEQ ID NO: 2 is substituted by atc and encodes the amino acid sequence shown in SEQ ID NO: 7, wherein alanine at position 26 of the amino acid sequence shown in SEQ ID NO: 1 is substituted by isoleucine) (DNA consisting of the nucleotide sequence shown in SEQ ID NO: 28) and DNA consisting of the nucleotide sequence at positions 65 to 87 of the nucleotide sequence shown in SEQ ID NO: 8 (DNA consisting of the nucleotide sequence shown in SEQ ID NO: 29) were synthesized using a DNA synthesizer.

The same procedure as in Example 1 (2) was carried out except that the DNAs consisting of the nucleotide sequences shown in SEQ ID NOS: 26 and 27 were used in place of the DNAs consisting of the nucleotide sequences shown in SEQ ID NOS: 15 and 16 to obtain a ca. 1.0 kb DNA fragment having DNA having the nucleotide sequence shown in SEQ ID NO: 6. Separately, the same procedure as in Example 1 (2) was carried out except that the DNAs consisting of the nucleotide sequences shown in SEQ ID NOS: 28 and 29 were used in place of the DNAs consisting of the nucleotide sequences shown in SEQ ID NOS: 15 and 16 to obtain a ca. 1.0 kb DNA fragment having DNA having the nucleotide sequence shown in SEQ ID NO: 8.

The same procedure as in Example 1 (4) was carried out except that the DNA fragments respectively having DNAs having the nucleotide sequences shown in SEQ ID NOS: 6 and 8 were used in place of the DNA fragments respectively having DNAs having the nucleotide sequences shown in SEQ ID NOS: 4 and 10 to obtain plasmids in which the DNAs having the nucleotide sequences shown in SEQ ID NOS: 6 and 8 were respectively incorporated into plasmid pESB30-T. The obtained plasmids were designated as pEargB26L and pEargB26I, respectively.

(2) Introduction of Substitution of One Amino Acid in ArgB into a Strain Having a Deletion of an Internal Sequence of ArgR The same procedure as in Example 2 (1) was carried out except that the strain R was used as a host and pEargB26L and pEargB26I were used as plasmids. This procedure yielded a strain in which the DNA encoding ArgB on the chromosome of the strain R was substituted by the DNA having the nucleotide sequence shown in SEQ ID NO: 6 and a strain in which the DNA encoding ArgB on the chromosome of the strain R was substituted by the DNA having the nucleotide sequence shown in SEQ ID NO: 8. The obtained strains were designated as strain RB26L and strain RB26I, respectively.

(3) L-Arginine, L-Ornithine and L-Citrulline Production Test Using Strains Having an Amino Acid Substitution in ArgB and a Deletion of an Internal Sequence of ArgR The productivity of L-arginine, L-ornithine and L-citrulline was examined in the same manner as in Example 3 except that the strains RB26, RB26L and RB26I were used.

The results are shown in Table 3.

TABLE 3

| Strain | OD 660 nm | L-Arginine (g/l) | L-Ornithine (g/l) | L-Citrulline (g/l) |
|---|---|---|---|---|
| ATCC 13032 | 48 | 0.0 | 0.0 | 0.0 |
| RB26 | 43 | 3.0 | 0.2 | 1.0 |
| RB26L | 41 | 3.3 | 0.3 | 1.2 |
| RB26I | 41 | 4.1 | 0.4 | 1.8 |

As is clear from Table 3, both of the strain RB26L having the DNA having the nucleotide sequence shown in SEQ ID NO: 6 and the strain RB26I having the DNA having the nucleotide sequence shown in SEQ ID NO: 8 produced L-arginine, L-ornithine and L-citrulline as well as the strain RB26 having the DNA having the nucleotide sequence shown in SEQ ID NO: 4. The amounts of these amino acids produced by using the strains RB26L and RB26I were higher than those by using the strain RB26.

Example 7

L-Citrulline Production Using Strains Having an Amino Acid Substitution in ArgB and a Deletion of an Internal Sequence of ArgG Primers are synthesized based on the nucleotide sequence shown in SEQ ID NO: 32 containing the nucleotide sequence of DNA encoding ArgG of *Corynebacterium glutamicum*. PCR is carried out using the obtained primers and the chromosomal DNA of *Corynebacterium glutamicum* ATCC 13032 as a template to construct a plasmid containing a DNA fragment having a deletion of about 400 base pairs in the DNA encoding ArgG.

A DNA fragment having a deletion of about 400 base pairs in the DNA encoding ArgG is prepared from the plasmid, and one adenine base is added to the 3' end of the DNA fragment. Ligase reaction is carried out using pESB30-T prepared in Example 1, the DNA fragment having the added adenine and Ligation Kit Ver. 1 (Takara Shuzo Co., Ltd.), and the obtained plasmid is designated as pEargG.

The above process can be carried out according to the method described in Example 4.

The same procedure as in Example 2 (1) is carried out except that the strains B26, B31, R, RB26, RB31 and ATCC 13032 are used as hosts and pEargG is used as a plasmid. This procedure yields strains in which the DNA encoding ArgG on the chromosome is substituted by the DNA wherein 400 base pairs in the DNA encoding ArgG are deleted, and the obtained strains are designated as strains GB26, GB31, GR, GRB26, GRB31 and G, respectively.

The strains GB26, GB31, GR, GRB26, GRB31, G and ATCC 13032 are separately cultured on BY agar medium at 30° C. for 24 hours. Each of the strains is inoculated into a test tube containing 6 ml of a seed medium (a medium which is prepared by adding 10 g of calcium carbonate to a medium containing 25 g of glucose, 0.5 g of potassium dihydrogenphosphate, 1.5 g of dipotassium hydrogenphosphate, 0.5 g of magnesium sulfate, 20 g of peptone, 3 g of urea, 50 µg of biotin and 0.3 g of L-arginine in 1 liter of water), followed by shaking culture at 32° C. for 24 hours. Each of the obtained seed cultures (2 ml) is inoculated into a flask with baffles containing 20 ml of a main culture medium (a medium which is prepared by adding 30 g of calcium carbonate to a medium containing 100 g of glucose, 30 g of ammonium sulfate, 0.6 g of magnesium sulfate, 0.5 g of potassium dihydrogenphosphate, 0.25 g of L-arginine, 16 mg of iron sulfate heptahydrate, 16 mg of manganese sulfate pentahydrate, 4.9 mg of zinc sulfate heptahydrate, 4.9 mg of copper sulfate pentahydrate, 16 mg of calcium chloride, 16 mg of β-alanine, 8 mg of thiamine hydrochloride, 180 µg of biotin and 16 g of corn steep liquor in 930 ml of water and adjusted to pH 7.2 with an aqueous solution of sodium hydroxide), followed by shaking culture at 32° C. for 48 hours.

After the cells are removed from the culture by centrifugation, the amount of L-citrulline accumulated in the supernatant is determined by high performance liquid chromatography (HPLC).

INDUSTRIAL APPLICABILITY

In accordance with the present invention, modified N-acetylglutamate kinase and DNA encoding the modified N-acetylglutamate kinase are provided, and L-arginine, L-ornithine or L-citrulline can be efficiently produced by using a microorganism having the DNA.

Sequence Listing Free Text

SEQ ID NO: 13—Description of Artificial Sequence: Synthetic DNA
SEQ ID NO: 14—Description of Artificial Sequence: Synthetic DNA
SEQ ID NO: 15—Description of Artificial Sequence: Synthetic DNA
SEQ ID NO: 16—Description of Artificial Sequence: Synthetic DNA
SEQ ID NO: 17—Description of Artificial Sequence: Synthetic DNA
SEQ ID NO: 18—Description of Artificial Sequence: Synthetic DNA
SEQ ID NO: 20—Description of Artificial Sequence: Synthetic DNA
SEQ ID NO: 21—Description of Artificial Sequence: Synthetic DNA
SEQ ID NO: 22—Description of Artificial Sequence: Synthetic DNA
SEQ ID NO: 23—Description of Artificial Sequence: Synthetic DNA
SEQ ID NO: 24—Description of Artificial Sequence: Synthetic DNA
SEQ ID NO: 25—Description of Artificial Sequence: Synthetic DNA
SEQ ID NO: 26—Description of Artificial Sequence: Synthetic DNA
SEQ ID NO: 27—Description of Artificial Sequence: Synthetic DNA
SEQ ID NO: 28—Description of Artificial Sequence: Synthetic DNA
SEQ ID NO: 29—Description of Artificial Sequence: Synthetic DNA

The invention claimed is:

1. A process for producing L-arginine, L-ornithine or L-citrulline, comprising the steps of:
   culturing in a medium an isolated microorganism carrying a DNA comprising a nucleotide sequence selected from the group consisting of SEQ ID NOS: 4, 6, 8, 10 and 12;
   allowing L-arginine, L-ornithine or L-citrulline to form and accumulate in the medium; and
   recovering L-arginine, L-ornithine or L-citrulline from the medium.

2. A process for producing L-arginine, L-ornithine or L-citrulline, comprising the steps of:
   culturing in a medium an isolated microorganism carrying a DNA which hybridizes with DNA consisting of a nucleotide sequence complementary to the nucleotide sequence of DNA encoding SEQ ID NO: 1 at 65° C. in 0.7-1.0 mol/l sodium chloride followed by washing at 65° C. with 0.1-2 ×SSC solution, said DNA being selected from the group consisting of the following (i) to (iii):
   (i) DNA encoding a polypeptide wherein the amino acid residue corresponding to the residue at position 26 from the N terminus of the amino acid sequence shown in SEQ ID NO: 1 is an amino acid residue other than L-alanine;
   (ii) DNA encoding a polypeptide wherein the amino acid residue corresponding to the residue at position 31 from the N terminus of the amino acid sequence shown in SEQ ID NO: 1 is an amino acid residue other than L-methionine; and
   (iii) DNA encoding a polypeptide wherein the amino acid residue corresponding to the residue at position 26 from the N terminus of the amino acid sequence shown in SEQ ID NO: 1 is an amino acid residue other than L-alanine and the amino acid residue corresponding to the residue at position 31 is an amino acid residue other than L-methionine, and
   which encodes a polypeptide having N-acetylglutamate kinase activity;
   allowing L-arginine, L-ornithine or L-citrulline to form and accumulate in the medium; and
   recovering L-arginine, L-ornithine or L-citrulline from the medium.

3. The process according to claim 2, wherein the amino acid residue corresponding to the residue at position 26 from the N terminus of the amino acid sequence shown in SEQ ID NO: 1 is L-valine, L-leucine or L-isoleucine and the amino acid residue corresponding to the residue at position 31 is L-valine.

4. A process for producing L-arginine, L-ornithine or L-citrulline, comprising the steps of:
   culturing in a medium an isolated microorganism carrying a DNA which hybridizes with DNA consisting of a nucleotide sequence complementary to the nucleotide sequence of DNA encoding SEQ ID NO: 1 at 65° C. in 0.7-1.0 mol/l sodium chloride followed by washing at 65° C with 0.1-2 ×SSC solution, selected from the group consisting of the following (i) to (iii):
   (i) DNA having a nucleotide sequence wherein the region corresponding to the region at positions 76 to 78 from the 5' end of the nucleotide sequence shown in SEQ ID NO: 2 is guanine-thymidine-thymidine, cytosine-thymidine-guanine or adenine-thymidine-cytosine;
   (ii) DNA having a nucleotide sequence wherein the region corresponding to the region at positions 91 to 93 from the 5' end of the nucleotide sequence shown in SEQ ID NO: 2 is guanine-thymidine-guanine; and
   (iii) DNA having a nucleotide sequence wherein the region corresponding to the region at positions 76 to 78 from the 5' end of the nucleotide sequence shown in SEQ ID NO: 2 is guanine-thymidine-thymidine, cytosine-thymidine-guanine or adenine-thymidine-cytosine, and the region corresponding to the region at positions 91 to 93 is guanine-thymidine-guanine; and
   which encodes a polypeptide having N-acetylglutamate kinase activity;
   allowing L-arginine, L-ornithine or L-citrulline to form and accumulate in the medium; and
   recovering L-arginine, L-ornithine or L-citrulline from the medium.

5. A process according to any one of claims 1-4, wherein said DNA is a recombinant DNA obtained by incorporating said DNA into a vector.

6. The process according to claim 5, wherein the transcriptional repression activity of the arginine repressor on the arginine operon is reduced or lost.

7. The process according to claim 6, wherein ornithine carbamoyl transferase activity is reduced or lost.

8. The process according to claim 7, wherein argininosuccinate synthase activity is reduced or lost.

9. The process according to claim 8, wherein the microorganism belonging belongs to the genus *Corynebacterium*.

10. The process according to claim 9, wherein the microorganism is *Corynebacterium glutamicum*.

* * * * *

UNITED STATES PATENT AND TRADEMARK OFFICE
CERTIFICATE OF CORRECTION

| | | |
|---|---|---|
| PATENT NO. | : 7,741,081 B2 | Page 1 of 1 |
| APPLICATION NO. | : 11/575805 | |
| DATED | : June 22, 2010 | |
| INVENTOR(S) | : Masato Ikeda et al. | |

It is certified that error appears in the above-identified patent and that said Letters Patent is hereby corrected as shown below:

COLUMN 4

Line 15, "to the" should read --to any one of the--.

COLUMN 15

Line 37, "DATP" should read --dATP--.

COLUMN 20

Line 30, "DATP" should read --dATP--.

COLUMN 21

Line 7, "180 a g" should read --180 µg--.

COLUMN 64

Line 56, "belonging" should be deleted.

Signed and Sealed this

Seventh Day of September, 2010

David J. Kappos
*Director of the United States Patent and Trademark Office*